US010946077B2

(12) United States Patent
Geldhof et al.

(10) Patent No.: US 10,946,077 B2
(45) Date of Patent: Mar. 16, 2021

(54) COOPERIA VACCINE

(71) Applicant: Universiteit Gent, Ghent (BE)

(72) Inventors: Peter Geldhof, Anzegem (BE); Jimmy Borloo, Ghent (BE); Edwin Claerebout, Lokeren (BE); Jozef Vercruysse, Ghent (BE)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 16/126,536

(22) Filed: Sep. 10, 2018

(65) Prior Publication Data

US 2018/0369349 A1 Dec. 27, 2018

Related U.S. Application Data

(63) Continuation of application No. 14/434,111, filed as application No. PCT/EP2013/070903 on Oct. 8, 2013, now Pat. No. 10,105,424.

(30) Foreign Application Priority Data

Oct. 9, 2012 (EP) .................................... 12187773

(51) Int. Cl.
*C12N 15/00* (2006.01)
*A61K 39/00* (2006.01)
*C07K 14/435* (2006.01)
*A61K 38/17* (2006.01)

(52) U.S. Cl.
CPC ...... *A61K 39/0003* (2013.01); *C07K 14/4354* (2013.01); *A61K 38/1767* (2013.01); *A61K 2039/545* (2013.01); *A61K 2039/552* (2013.01)

(58) Field of Classification Search
None
See application file for complete search history.

(56) References Cited

U.S. PATENT DOCUMENTS

| 5,084,269 | A | 1/1992 | Kullenberg | |
|---|---|---|---|---|
| 5,961,970 | A | 10/1999 | Lowell et al. | |
| 6,071,518 | A | 6/2000 | Petersen | |
| 8,580,272 | B2 | 11/2013 | Liu et al. | |
| 9,078,841 | B2 * | 7/2015 | Smith | A61K 39/0003 |
| 10,105,424 | B2 * | 10/2018 | Geldhof | C07K 14/4354 |
| 2005/0220814 | A1 | 10/2005 | Dominowski et al. | |
| 2009/0325204 | A1 | 12/2009 | Reed et al. | |
| 2015/0265687 | A1 * | 9/2015 | Geldhof | C07K 14/4354 424/191.1 |
| 2018/0369349 | A1 * | 12/2018 | Geldhof | C07K 14/4354 |

FOREIGN PATENT DOCUMENTS

| EP | 473210 A2 | 3/1992 | | |
|---|---|---|---|---|
| EP | 2906588 B1 * | 12/2018 | ......... | A61K 39/0003 |
| ES | 2717441 T3 * | 6/2019 | ......... | A61K 39/0003 |
| WO | 9213889 A1 | 8/1992 | | |
| WO | 9801550 A2 | 1/1998 | | |
| WO | 2011073630 A2 | 6/2011 | | |
| WO | WO-2014056885 A1 * | 4/2014 | | |

OTHER PUBLICATIONS

Borloo et al., Journal Proteome Research, 2013, 12:3900-3911, published: Jul. 29, 2013 (Year: 2013).*
Gonzalez-Hernandez et al, International Journal for Parasitology, 2018, 48:41-49. Available online: Aug. 30, 2017 (Year: 2018).*
Van Meulder et al, International J. Parasitology, 2015, 45:637-646. available online: May 1, 2015 (Year: 2015).*
Vlaminck et al, International J. Parasitology, 2015, 45:209-213. available online: Dec. 13, 2014 (Year: 2015).*
Yatsuda et al, Vet. Parasitology, 2002, 105:131-138 (Year: 2002).*
What are DNA Vaccines? Biology.Kenyon.edu/slonc/bio38/scuderi/partii.html (Year: 2011).*
Vogel et al, Clinical Mircobiol. Review, Jul. 1995, 8/3:406-410 (Year: 1995).*
Ferraao et al, Clinical Infectious Diseases, Aug. 1, 2011, 53/3:296-302 (Year: 2011).*
Burgess et al., JCB, 1990, 111:2129-2138 (Year: 1990).
Lazar et al. Molecular and Cellular Biology, 1988, 8:1247-1252 (Year: 1988).
Greenspan et al. Nature Biotechnology 17:936-937, 1999 (Year: 1999).
Blythe et al. Protein Science, 2005, 14:246-248 (Year: 2005).
Houghten et al (Vaccine 86, 1986, pp. 21-25) (Year: 1986).
Bixler et al. Synthetic Vaccines, vol. 1, 1987, pp. 39-71 (Year: 1987).
Bowie et al. Science, 1990, vol. 247:1306-1310 (Year: 1990).
Kumar et al. PNAS 87: 1337-1341 Feb. 1991 (Year: 1991).
Asojo, et al., X-ray Structure of Na-ASP-2, a Pathogenesis-related-1 Protein from the Mematode Parasite, *Necator americanus*, and a Vaccine Antigen for Human Hookworm Infection, J. Mol. Biol., 2005, pp. 801-814, vol. 10, Elsevier Ltd., USA.
Asojo, Structure of a Two-CAP-Domain Protein From the Human Hookworm Parasite *Necator americanus*, 2011 International Union of Crystallography, pp. 455-462, Section D, Singapore, China.
El-Abdellati, et al., Monitoring Macrocyclic Lactone Resistance in Cooperia Oncophora on a Belgian Cattle Farm During Four Consecutive Years, Veterinary Parasitology, 2010, pp. 167-171, vol. 171, Belgium.
Elliott, et al., Helminths as Governors of Immune-Mediated Inflammation, International Journal for Parasitology, 2007, pp. 457-464, vol. 37, www.sciencedirect.com, Australia.

(Continued)

*Primary Examiner* — Nita M. Minnifield
(74) *Attorney, Agent, or Firm* — Dinsmore & Shohl LLP

(57) ABSTRACT

The present invention relates to nucleotide sequences encoding *Cooperia* antigens, as well as to recombinant DNA molecules containing such nucleotide sequences and host cells expressing these nucleotide sequences. The invention further relates to *Cooperia* proteins, to methods for the production of the proteins, nucleotide sequences, recombinant DNA molecules and hosts. Furthermore, the invention relates to vaccines which induce protective immunity against infection by parasitic nematodes such as species of the genus *Cooperia* and to methods for preparing such a vaccine.

11 Claims, 7 Drawing Sheets

Specification includes a Sequence Listing.

(56) References Cited

OTHER PUBLICATIONS

Geldhof, et al., Recombinant Expression Systems: The Obstacle to Helminth Vaccines?, ScienceDirect, 2007, vol. 23, No. 11, pp. 527-532, Belgium.

Geldhof, et al. Vaccination of Calves Against Ostertagia Ostertagi with Cysteine Proteinase Enriched Protein Fractions, Parasite Immunology, 2002, vol. 24, pp. 263-270, Blackwell Science Ltd., Belgium.

Geldhof, et al., Activation-Associated Secreted Proteins Are the Most Abundant Antigens in a Host Protective Fraction From Ostertagia Ostertagi, Science Direct, Molecular & Biochemical Parasitology, 2003, vol. 128, pp. 111-114, Elsevier Science B.V., Belgium.

Geldhof, et al., Vaccine Testing of a Recombinant Activation-Associated Secreted Protein (ASP1) from Ostertagia Ostertagi, Parasite Immunology, 2008, vol. 30, pp. 57-60, Blackwell Publishing Ltd., Belgium.

Gibbs, et al., The CAP Superfamily: Cysteine-Rich Secretory Proteins, Antigen 5, and Pathogenesis-Related 1 Proteins—Roles in Reproduction, Cancer, and Immune Defense, The Endocrine Society, 2008, vol. 29, No. 7, pp. 865-897, Australia.

Goud, et al., Cloning, Yeast Expression, Isolation, and Vaccine Testing of Recombinant Ancylostoma-Secreted Protein (ASP-1) and ASP-2 from Ancylostoma Ceylanicum, JID, 2004, vol. 1, No. 89, pp. 919-929, USA.

Hawdon, et al., Cloning and Characterization of Ancylostomoa-secreted Protein, The Journal of Biological Chemistry, 1996, vol. 271, No. 12, pp. 6672-6678, USA.

Kanobana, et al., T-Cell Mediated Immune Responses in Calves Primary-Infected or Re-Infected With Cooperia Oncophora: Similar Effector Cells But Different Timing, International Journal for Parasitology, 2003, vol. 33, pp. 1503-1514, Elsevier Ltd., Australia.

Kloosterman, et al., Negative Interactions Between Ostertagia Ostertagi and Cooperia Oncophora in Calves, Veterinary Parasitology, 1984, vol. 15, pp. 135-150, Elsevier Science Publishers B.V., The Netherlands.

Mendez, et al., Effect of Combining the Larval Antigens Ancylostoma Secreted Protein 2 (ASP-2) and Metalloprotease 1 (MTP-1) in Protecting Hamsters Against Hookworm Infection and Disease Caused by Ancylostoma Ceylanicum, Science Direct, 2005, vol. 23, pp. 3123-3130, Elsevier Ltd., USA.

Meyvis, et al., Vaccination Against Ostertagia Ostertagi With Subfractions of the Protective ES-Thiol Fraction, Veterinary Parasitology, 2007, vol. 149, pp. 239-245, Elsevier B.V., Belgium.

Osman, et al., Hookworm SCP/TAPS Protein Structure—A Key to Understanding Host-Parasite Interactions and Developing New Interventions, Biotechnology Advances, 2012, vol. 30, pp. 652-657, Elsevier Inc., USA.

Kooyman, et al., Identification of a Thrombospondin-Like Immunodominant and Phosphorylcholine-Containing Glycoprotein (GP300) in Dictyocaulus Viviparus and Related Nematodes, Molecular & Biochemical Parasitology, 2009, vol. 163, pp. 85-94, Elsevier B.V., The Netherlands.

Poot, et al., Use of Cloned Excretory/Secretory Low-Molecular-Weight Proteins of Cooperia Oncophora in a Serological Assay, Journal of Clinical Microbiology, 1997, vol. 35, No. 7, pp. 1728-1733, American Society for Microbiology, USA.

Li, et al., Localized Complement Activation in the Development of Protective Immunity Against Ostertagia Ostertagi Infections in Cattle, Veterinary Parasitology, 2010, vol. 174, pp. 247-256, Elsevier B.V., The Netherlands.

Abubucker, et al., The Transcriptomes of the Cattle Parasitic Nematode Ostertagia Ostartagi, Veterinary Parasitology, 2009, vol. 162, pp. 89-99, Elsevier B.V., The Netherlands.

Yatsuda, et al., A Family of Activation Associated Secreted Protein (ASP) Homologues of Cooperia Punctata, Research in Veterinary Science, 2002, vol. 73, pp. 297-306, Elsevier Science Ltd., The Netherlands.

Yatsuda, et al., A Cooperia Punctata Gene Family Encoding 14 kDa Excretory-Secretory Antigens Conserved for Trichostrongyloid Nematodes, parasitology, 2001, vol. 123, pp. 631-639, Cambridge University Press, U.K.

International Search Report pertaining to Application No. PCT/GB2010/002298.

Villa-Mancera et al., "Induction of immunity in sheep to Fasciola hepatica with mimotopes of cathepsin L selected from a phage display library", Parasitology, 2008 Cambridge University Press, UK, pp. 1437-1445.

Villa-Mancera et al., "Protection and antibody isotype responses against Fasciola hepatica with specific antibody to pIII-displayed peptide mimotopes of cathepsin L1 in sheep", The Veterinary Journal 194, 2012, pp. 108-112.

Villa-Mancera et al., "Cathepsin L1 mimotopes with adjuvant Quil A induces a Th1/Th2 immune response and confers significant protection against Fasciola hepatica infection in goats", Parasitol Res, Mexico, 2014, 113:243-250.

* cited by examiner

Figure 1

A. Double-domain ASP variant A

DEIRKVFLDKHNEYRSLVAKGQALNPQFGGSTPKAARMLKARYDCDVEEDMTKWAQAQCTYAPFKSSKRYGRNT
WGMGVPNYNKTAAAESSVYDWFFELRRYGVPQDNVYTRDVDYSAYHYAQMVWQDSYKIGCVVAWCPSMTWV
ACGYSPAGDNIGSLIYELGEPCTKNEDCKCTDCTCSEGEALCIPPGGPKPATTASTTTKTTTTTKPTTTTTEPSTTTA
KPTTTFDRAAWEESVKRPVARCTLDNGMTDEARQVFLDKHNEYRQLVARGEAKNKTGLAPPAARMLQMRYDC
DLEAHVMEHVKQCKGGHSSFDVLKGRGQNIWAITVPNLDKADAANRSVHDWYIELTKYGITADNKISMDNAANT
GHYSQVVWQKSNRLGCAAVSCPEQGKLFVGCEYLPGGNTLHHLIYDIGEPCKR (SEQ ID NO: 1)

GATGAGATCAGAAAAGTCTTCCTTGACAAGCACAATGAGTACCGGTCACTCGTTGCTAAAGGACAGGCTCTGAAT
CCACAGTTTGGCGGGTCTACTCCAAAGGCCGCTAGAATGCTCAAAGCGAGGTACGATTGCGATGTTGAAGAAGAC
ATGACGAAGTGGGCTCAAGCGCAGTGCACGTACGCACCATTCAAAAGTAGCAAACGTTACGGCCGGAACACATGG
GGCATGGGTGTCCCTAACTACAACAAGACAGCAGCTGCAGAATCGAGTGTTTACGACTGGTTCTTCGAACTACGG
CGCTATGGTGTTCCTCAAGATAACGTGTATACAAGAGATGTTGACTACAGTGCTTATCATTACGCTCAGATGGTT
TGGCAAGATAGTTACAAAATTGGATGTGTCGTGGCATGGTGTCCAAGCATGACCTGGGTAGCATGCGGATACAG
TCCAGCAGGAGATAATATCGGATCCCTAATTTACGAGCTTGGAGAACCGTGTACAAAGAATGAAGACTGTAAAT
GCACCGACTGCACATGTAGTGAAGGAGAAGCTCTTTGTATACCTCCTGGAGGACCGAAACCCGCTACCACTGCAA
GCACCACGACCAAGACAACGACCACTACAAAGCCTACGACGACGACGACGGAACCTTCGACCACTACGGCGAAGC
CAACGACGACCTTCGATAGAGCTGCGTGGGAGGAGTCGGTCAAGAGGCCAGTAGCGCGTTGCACTCTTGACAACG
GAATGACAGACGAGGCCAGGCAGGTTTTCCTTGACAAGCACAACGAGTACCGGCAACTAGTTGCAAGAGGAGAA
GCTAAAAACAAGACAGGATTGGCTCCGCCGGCAGCTAGAATGCTACAAATGAGGTACGATTGCGACCTTGAGGCA
CATGTTATGGAGCACGTTAAACAGTGTAAAGGCGGACATTCATCATTTGATGTGCTTAAAGGTAGGGGGCAGAA
CATATGGGCCATAACTGTCCCTAACTTGGACAAGGCTGATGCTGCAAACCGGAGTGTCCATGACTGGTACATCGA
ATTAACGAAATATGGTATAACCGCAGATAACAAGATATCAATGGACAATGCTGCAAACACTGGTCATTACTCGC
AGGTAGTTTGGCAAAAGTCGAACAGACTTGGATGTGCAGCGGTGTCCTGTCCAGAACAAGGAAAACTCTTTGTA
GGTTGCGAATATTTACCAGGAGGGAACACACTTCACCATCTGATTTACGATATCGGAGAGCCATGCAAACGG
(SEQ ID NO: 2)

B. Double-domain ASP variant B

DEIRKVFLDKHNEYRSLVAKGQAPNPQFGGSTPKAARMLKAMYDCDVEEDMTKWAQAQCTYAPFKSSKHYGRN
TWGMGVPNYNKTAAAESSVYDWFSELRRYGVPQDNVYTRDVDYSAYQYAQMVWQDSYKIGCVVAWCPSVTWV
ACGYSPAGDNIGSLIYELGEPCTKNEDCKCTDCTCSEGEALCIPPGGPKPATTASTTTKTTTTTKPTTTTTKLSTTT
AKPTTTFDRAAWEESVKRPVARCTLDNGMTDEARQVFLDKHNEYRQLVARGEAKNKTGLAPPAARMLQMRYD
CDLEAHVMEHVKQCKGGHSSFDVLKGRGQNIWAITVPNLDKADAANRSVHDWYIELTKYGITADNKISMDNAAN
TGHYSQVVWQKSNRLGCAAVSCPEQGKLFVGCEYLPGGNTLHHLIYDIGEPCKR (SEQ ID NO: 3)

Figure 1 continued

GATGAGATCAGGAAAGTCTTCCTTGACAAGCACAATGAGTATCGGTCACTCGTTGCTAAAGGACAGGCTCCGAAT
CCACAGTTTGGCGGATCTACTCCAAAGGCCGCTAGAATGCTCAAAGCGATGTACGATTGCGATGTTGAAGAAGAC
ATGACGAAGTGGGCTCAAGCGCAGTGCACGTACGCACCATTCAAAAGTAGCAAACATTACGGCCGGAACACATGG
GGCATGGGTGTCCCTAACTACAACAAGACAGCAGCTGCAGAATCGAGTGTTTACGACTGGTTCTCCGAACTACGG
CGCTATGGTGTTCCTCAAGATAACGTGTATACAAGAGATGTTGACTACAGTGCTTATCAATACGCTCAGATGGTT
TGGCAAGACAGTTACAAAATTGGATGTGTCGTGGCATGGTGTCCAAGCGTGACCTGGGTAGCGTGCGGATACAGT
CCAGCAGGAGATAATATCGGATCCCTAATTTACGAGCTTGGAGAACCGTGTACGAAGAATGAAGACTGTAAATG
CACCGACTGCACATGTAGTGAAGGAGAAGCTCTTTGTATACCTCCTGGAGGACCAAAACCCGCTACCACTGCAAG
CACCACAACCAAGACAACGACCACTACAAAGCCTACGACGACGACGACGAAACTTTCGACCACTACGGCGAAGCC
AACGACGACCTTCGATAGAGCTGCGTGGGAGGAGTCGGTCAAGAGGCCAGTAGCGCGTTGCACTCTTGACAACGG
AATGACAGACGAGGCCAGGCAGGTTTTCCTTGACAAGCACAACGAGTACCGACAACTAGTTGCAAGAGGAGAAG
CTAAAAACAAGACAGGATTGGCTCCGCCGGCAGCTAGAATGCTACAAATGAGGTACGATTGCGACCTTGAGGCAC
ATGTTATGGAGCACGTTAAACAATGTAAAGGCGGACATTCATCATTTGATGTGCTTAAAGGTAGGGGGCAGAAC
ATATGGGCCATAACTGTCCCTAACTTGGACAAGGCTGATGCTGCAAACCGGAGTGTCCATGACTGGTACATCGAA
TTAACGAAATATGGTATAACTGCAGATAACAAGATATCAATGGACAATGCTGCAAACACTGGTCATTACTCGCA
GGTAGTTTGGCAAAAGTCGAACAGACTTGGATGTGCAGCGGTGTCCTGTCCAGAACAAGGAAAACTCTTTGTAG
GTTGCGAATATTTACCAGGAGGGAACACACTTCACCATCTGATTTACGATATCGGAGAGCCATGCAAACGG (SEQ
ID NO: 4)

C. Double-domain ASP variant C

DEIRKVFLDKHNEYRSLVAKGQAPNPQFGGSTPKAARMLKARYDCDVEEDMTKWAQAQCTYAPFKSSKRYGRNT
WGMGVPNYNKIAAAESSVDDWFFELRRYGVPQDNVYTRDVDYSAYHYAQMVWQDSYKIGCVVAWCPSMTWVA
CGYSPAGDNIGSLIYELGEPCTKNEDCKCTDCTCSEGEALCIPPGEPKPATTASTTTKTTTTTEPTTTTTEPSTTTAK
PTTTTFDRAAWEESVKRPVARCTLDNGMTDEARQVFLDKHNEYRQLVARGEAKNKTGLAPPAARMLQMRYDCD
LEAHVMEHVKQCKGGHSSFDVLKGRGQNIWAITVPNLDKADAANRSVHDWYIELTKYGITADNKISMDNAANTG
HYSQVVWQKSNRLGCAAVSCPEQGKLFVGCEYLPGGNTLHHLIYDIGEPCKR (SEQ ID NO: 5)

GATGAGATCAGAAAAGTCTTCCTTGACAAGCACAATGAGTATCGGTCACTCGTTGCTAAAGGACAGGCTCCGAAT
CCACAGTTTGGCGGGTCTACTCCAAAGGCCGCTAGAATGCTCAAAGCGAGGTACGATTGCGATGTTGAAGAAGAC
ATGACGAAGTGGGCTCAAGCGCAGTGCACGTACGCACCATTCAAAAGTAGCAAACGTTACGGCCGGAACACATGG
GGAATGGGTGTCCCTAACTACAACAAGATAGCAGCTGCAGAATCGAGTGTTGACGACTGGTTCTTCGAACTACGG
CGCTATGGTGTTCCTCAAGATAACGTGTATACAAGAGATGTTGACTACAGTGCTTATCATTACGCTCAGATGGTT
TGGCAAGACAGTTACAAAATTGGATGTGTCGTGGCATGGTGTCCAAGCATGACCTGGGTAGCGTGCGGATACAGT
CCAGCAGGAGATAATATCGGATCCCTAATTTACGAGCTTGGAGAACCGTGTACAAGAATGAAGACTGTAAATG
CACCGACTGCACATGTAGTGAAGGAGAAGCTCTTTGTATACCTCCTGGAGAACCGAAACCCGCTACCACTGCAAG
CACCACGACCAAGACAACGACCACTACAGAGCCTACGACAACGACGACGGAACCGTCGACCACTACGGCGAAGCC
AACGACGACCTTCGATAGAGCTGCGTGGGAGGAGTCGGTCAAGAGGCCAGTAGCGCGTTGCACTCTTGACAACGG
AATGACAGACGAGGCCAGGCAGGTTTCCCTCGACAAGCACAACGAGTACCGGCAACTAGTTGCAAGAGGAGAAGC
TAAAAACAAGACAGGATTGGCTCCGCCGGCAGCTAGAATGCTACAAATGAGGTACGATTGCGACCTTGAGGCACA
TGTTATGGAGCACGTTAAACAATGTAAAGGCGGACATTCATCATTTGATGTGCTTAAAGGTAGGGGGCAGAACA
TATGGGCCATAACTGTCCCTAACTTGGACAAGGCTGATGCTGCAAACCGGAGTGTCCATGACTGGTACATCGAAT
TAACGAAATATGGTATAACTGCAGATAACAAGATATCAATGGACAATGCTGCAAACACTGGTCATTACTCGCAG
GTAGTTTGGCAAAAGTCGAACAGACTTGGATGTGCAGCGGTGTCCTGTCCAGAACAAGGAAAACTCTTTGTAGGT
TGCGAATATTTACCAGGAGGGAACACACTTCACCATCTGATTTACGATATCGGAGAGCCATGCAAACGG (SEQ ID
NO: 6)

Figure 1 continued

D. Double-domain ASP variants including N- and C-termini

Variant A

LCSLDNGMTDEIRKVFLDKHNEYRSLVAKGQALNPQFGGSTPKAARMLKARYDCDVEEDMTKWAQAQCTYAPF
KSSKRYGRNTWGMGVPNYNKTAAAESSVYDWFFELRRYGVPQDNVYTRDVDYSAYHYAQMVWQDSYKIGCVVA
WCPSMTWVACGYSPAGDNIGSLIYELGEPCTKNEDCKCTDCTCSEGEALCIPPGGPKPATTASTTTKTTTTTKPTT
TTTEPSTTTAKPTTTFDRAAWEESVKRPVARCTLDNGMTDEARQVFLDKHNEYRQLVARGEAKNKTGLAPPAA
RMLQMRYDCDLEAHVMEHVKQCKGGHSSFDVLKGRGQNIWAITVPNLDKADAANRSVHDWYIELTKYGITADN
KISMDNAANTGHYSQVVWQKSNRLGCAAVSCPEQGKLFVGCEYLPGGNTLHHLIYDIGEPCKR
DEDCKCSSCRCSTQLSMCINPN (SEQ ID NO: 16)

CTTTGCTCGCTTGATAATGGAATGACAGATGAGATCAGAAAAGTCTTCCTTGACAAGCACAATGAGTACCGGTCA
CTCGTTGCTAAAGGACAGGCTCTGAATCCACAGTTTGGCGGGTCTACTCCAAAGGCCGCTAGAATGCTCAAAGCG
AGGTACGATTGCGATGTTGAAGAAGACATGACGAAGTGGGCTCAAGCGCAGTGCACGTACGCACCATTCAAAAG
TAGCAAACGTTACGGCCGGAACACATGGGGCATGGGTGTCCCTAACTACAACAAGACAGCAGCTGCAGAATCGAG
TGTTTACGACTGGTTCTTCGAACTACGGCGCTATGGTGTTCCTCAAGATAACGTGTATACAAGAGATGTTGACTA
CAGTGCTTATCATTACGCTCAGATGGTTTGGCAAGATAGTTACAAAATTGGATGTGTCGTGGCATGGTGTCCAAG
CATGACCTGGGTAGCATGCGGATACAGTCCAGCAGGAGATAATATCGGATCCCTAATTTACGAGCTTGGAGAACC
GTGTACAAAGAATGAAGACTGTAAATGCACCGACTGCACATGTAGTGAAGGAGAAGCTCTTTGTATACCTCCTG
GAGGACCGAAACCCGCTACCACTGCAAGCACCACGACCAAGACAACGACCACTACAAAGCCTACGACGACGACGA
CGGAACCTTCGACCACTACGGCGAAGCCAACGACGACCTTCGATAGAGCTGCGTGGGAGGAGTCGGTCAAGAGGC
CAGTAGCGCGTTGCACTCTTGACAACGGAATGACAGACGAGGCCAGGCAGGTTTTCCTTGACAAGCACAACGAGT
ACCGGCAACTAGTTGCAAGAGGAGAAGCTAAAAACAAGACAGGATTGGCTCCGCCGGCAGCTAGAATGCTACAA
ATGAGGTACGATTGCGACCTTGAGGCACATGTTATGGAGCACGTTAAACAGTGTAAAGGCGGACATTCATCATTT
GATGTGCTTAAAGGTAGGGGGCAGAACATATGGGCCATAACTGTCCCTAACTTGGACAAGGCTGATGCTGCAAAC
CGGAGTGTCCATGACTGGTACATCGAATTAACGAAATATGGTATAACCGCAGATAACAAGATATCAATGGACAA
TGCTGCAAACACTGGTCATTACTCGCAGGTAGTTTGGCAAAAGTCGAACAGACTTGGATGTGCAGCGGTGTCCTG
TCCAGAACAAGGAAAACTCTTTGTAGGTTGCGAATATTTACCAGGAGGGAACACACTTCACCATCTGATTTACGA
TATCGGAGAGCCATGCAAACGGGATGAAGATTGTAAGTGCAGCTCCTGCAGATGCAGCACACAATTATCCATGTG
TATCAACCCTAAC (SEQ ID NO: 19)

Variant B

LCSLDNGMTDEIRKVFLDKHNEYRSLVAKGQAPNPQFGGSTPKAARMLKAMYDCDVEEDMTKWAQAQCTYAPF
KSSKHYGRNTWGMGVPNYNKTAAAESSVYDWFSELRRYGVPQDNVYTRDVDYSAYQYAQMVWQDSYKIGCVVA
WCPSVTWVACGYSPAGDNIGSLIYELGEPCTKNEDCKCTDCTCSEGEALCIPPGGPKPATTASTTTKTTTTTKPTT
TTTKLSTTTAKPTTTFDRAAWEESVKRPVARCTLDNGMTDEARQVFLDKHNEYRQLVARGEAKNKTGLAPPAA
RMLQMRYDCDLEAHVMEHVKQCKGGHSSFDVLKGRGQNIWAITVPNLDKADAANRSVHDWYIELTKYGITADN
KISMDNAANTGHYSQVVWQKSNRLGCAAVSCPEQGKLFVGCEYLPGGNTLHHLIYDIGEPCKR
DEDCKCSSCRCSTQLSMCINPN (SEQ ID NO: 17)

Figure 1 continued

CTTTGCTCGCTGGATAATGGAATGACAGATGAGATCAGGAAAGTCTTCCTTGACAAGCACAATGAGTATCGGTCA
CTCGTTGCTAAAGGACAGGCTCCGAATCCACAGTTTGGCGGATCTACTCCAAAGGCCGCTAGAATGCTCAAAGCG
ATGTACGATTGCGATGTTGAAGAAGACATGACGAAGTGGGCTCAAGCGCAGTGCACGTACGCACCATTCAAAAG
TAGCAAACATTACGGCCGGAACACATGGGGCATGGGTGTCCCTAACTACAACAAGACAGCAGCTGCAGAATCGAG
TGTTTACGACTGGTTCTCCGAACTACGGCGCTATGGTGTTCCTCAAGATAACGTGTATACAAGAGATGTTGACTA
CAGTGCTTATCAATACGCTCAGATGGTTTGGCAAGACAGTTACAAAATTGGATGTGTCGTGGCATGGTGTCCAAG
CGTGACCTGGGTAGCGTGCGGATACAGTCCAGCAGGAGATAATATCGGATCCCTAATTTACGAGCTTGGAGAACC
GTGTACGAAGAATGAAGACTGTAAATGCACCGACTGCACATGTAGTGAAGGAGAAGCTCTTTGTATACCTCCTGG
AGGACCAAAACCCGCTACCACTGCAAGCACCACAACCAAGACAACGACCACTACAAAGCCTACGACGACGACGAC
GAAACTTTCGACCACTACGGCGAAGCCAACGACGACCTTCGATAGAGCTGCGTGGGAGGAGTCGGTCAAGAGGCC
AGTAGCGCGTTGCACTCTTGACAACGGAATGACAGACGAGGCCAGGCAGGTTTTCCTTGACAAGCACAACGAGTA
CCGACAACTAGTTGCAAGAGGAGAAGCTAAAAACAAGACAGGATTGGCTCCGCCGGCAGCTAGAATGCTACAAA
TGAGGTACGATTGCGACCTTGAGGCACATGTTATGGAGCACGTTAAACAATGTAAAGGCGGACATTCATCATTTG
ATGTGCTTAAAGGTAGGGGGCAGAACATATGGGCCATAACTGTCCCTAACTTGGACAAGGCTGATGCTGCAAACC
GGAGTGTCCATGACTGGTACATCGAATTAACGAAATATGGTATAACTGCAGATAACAAGATATCAATGGACAAT
GCTGCAAACACTGGTCATTACTCGCAGGTAGTTTGGCAAAAGTCGAACAGACTTGGATGTGCAGCGGTGTCCTGT
CCAGAACAAGGAAAACTCTTTGTAGGTTGCGAATATTTACCAGGAGGGAACACACTTCACCATCTGATTTACGAT
ATCGGAGAGCCATGCAAACGGGATGAAGATTGTAAGTGCAGCTCCTGCAGATGCAGCACACAATTATCCATGTGT
ATCAACCCTAAC (SEQ ID NO: 20)

Variant C

LCSLDNGMTDEIRKVFLDKHNEYRSLVAKGQAPNPQFGGSTPKAARMLKARYDCDVEEDMTKWAQAQCTYAPF
KSSKRYGRNTWGMGVPNYNKIAAAESSVDDWFFELRRYGVPQDNVYTRDVDYSAYHYAQMVWQDSYKIGCVVA
WCPSMTWVACGYSPAGDNIGSLIYELGEPCTKNEDCKCTDCTCSEGEALCIPPGEPKPATTASTTTKTTTTTEPTT
TTTEPSTTTAKPTTTFDRAAWEESVKRPVARCTLDNGMTDEARQVFLDKHNEYRQLVARGEAKNKTGLAPPAA
RMLQMRYDCDLEAHVMEHVKQCKGGHSSFDVLKGRGQNIWAITVPNLDKADAANRSVHDWYIELTKYGITADN
KISMDNAANTGHYSQVVWQKSNRLGCAAVSCPEQGKLFVGCEYLPGGNTLHHLIYDIGEPCKR
DEDCKCSSCRCSTQLSMCINPN (SEQ ID NO: 18)

CTTTGCTCGCTGGATAATGGAATGACAGATGAGATCAGAAAAGTCTTCCTTGACAAGCACAATGAGTATCGGTCA
CTCGTTGCTAAAGGACAGGCTCCGAATCCACAGTTTGGCGGGTCTACTCCAAAGGCCGCTAGAATGCTCAAAGCG
AGGTACGATTGCGATGTTGAAGAAGACATGACGAAGTGGGCTCAAGCGCAGTGCACGTACGCACCATTCAAAAG
TAGCAAACGTTACGGCCGGAACACATGGGGAATGGGTGTCCCTAACTACAACAAGATAGCAGCTGCAGAATCGAG
TGTTGACGACTGGTTCTTCGAACTACGGCGCTATGGTGTTCCTCAAGATAACGTGTATACAAGAGATGTTGACTA
CAGTGCTTATCATTACGCTCAGATGGTTTGGCAAGACAGTTACAAAATTGGATGTGTCGTGGCATGGTGTCCAAG
CATGACCTGGGTAGCGTGCGGATACAGTCCAGCAGGAGATAATATCGGATCCCTAATTTACGAGCTTGGAGAACC
GTGTACAAAGAATGAAGACTGTAAATGCACCGACTGCACATGTAGTGAAGGAGAAGCTCTTTGTATACCTCCTG
GAGAACCGAAACCCGCTACCACTGCAAGCACCACGACCAAGACAACGACCACTACAGAGCCTACGACAACGACGA
CGGAACCGTCGACCACTACGGCGAAGCCAACGACGACCTTCGATAGAGCTGCGTGGGAGGAGTCGGTCAAGAGGC
CAGTAGCGCGTTGCACTCTTGACAACGGAATGACAGACGAGGCCAGGCAGGTTTCCCTCGACAAGCACAACGAGT
ACCGGCAACTAGTTGCAAGAGGAGAAGCTAAAAACAAGACAGGATTGGCTCCGCCGGCAGCTAGAATGCTACAA
ATGAGGTACGATTGCGACCTTGAGGCACATGTTATGGAGCACGTTAAACAATGTAAAGGCGGACATTCATCATT
TGATGTGCTTAAAGGTAGGGGGCAGAACATATGGGCCATAACTGTCCCTAACTTGGACAAGGCTGATGCTGCAAA
CCGGAGTGTCCATGACTGGTACATCGAATTAACGAAATATGGTATAACTGCAGATAACAAGATATCAATGGACA
ATGCTGCAAACACTGGTCATTACTCGCAGGTAGTTTGGCAAAAGTCGAACAGACTTGGATGTGCAGCGGTGTCCT
GTCCAGAACAAGGAAAACTCTTTGTAGGTTGCGAATATTTACCAGGAGGGAACACACTTCACCATCTGATTTACG
ATATCGGAGAGCCATGCAAACGGGATGAAGATTGTAAGTGCAGCTCCTGCAGATGCAGCACACAATTGTCCATGT
GTATCAACCCTAAC (SEQ ID NO: 21)

SEQUENCE LISTING

```
<160> NUMBER OF SEQ ID NOS: 21

<210> SEQ ID NO 1
<211> LENGTH: 422
<212> TYPE: PRT
<213> ORGANISM: Cooperia oncophora

<400> SEQUENCE: 1

Asp Glu Ile Arg Lys Val Phe Leu Asp Lys His Asn Glu Tyr Arg Ser
1               5                   10                  15

Leu Val Ala Lys Gly Gln Ala Leu Asn Pro Gln Phe Gly Gly Ser Thr
            20                  25                  30

Pro Lys Ala Ala Arg Met Leu Lys Ala Arg Tyr Asp Cys Asp Val Glu
        35                  40                  45

Glu Asp Met Thr Lys Trp Ala Gln Ala Gln Cys Thr Tyr Ala Pro Phe
    50                  55                  60

Lys Ser Ser Lys Arg Tyr Gly Arg Asn Thr Trp Gly Met Gly Val Pro
65                  70                  75                  80
```

Asn Tyr Asn Lys Thr Ala Ala Glu Ser Val Tyr Asp Trp Phe
            85                  90                  95

Phe Glu Leu Arg Arg Tyr Gly Val Pro Gln Asp Asn Val Tyr Thr Arg
                100                 105                 110

Asp Val Asp Tyr Ser Ala Tyr His Tyr Ala Gln Met Val Trp Gln Asp
            115                 120                 125

Ser Tyr Lys Ile Gly Cys Val Ala Trp Cys Pro Ser Met Thr Trp
130             135                 140

Val Ala Cys Gly Tyr Ser Pro Ala Gly Asp Asn Ile Gly Ser Leu Ile
145             150                 155                 160

Tyr Glu Leu Gly Glu Pro Cys Thr Lys Asn Glu Asp Cys Lys Cys Thr
                165                 170                 175

Asp Cys Thr Cys Ser Glu Gly Glu Ala Leu Cys Ile Pro Pro Gly Gly
            180                 185                 190

Pro Lys Pro Ala Thr Thr Ala Ser Thr Thr Lys Thr Thr Thr Thr
            195                 200                 205

Thr Lys Pro Thr Thr Thr Thr Glu Pro Ser Thr Thr Thr Ala Lys
210             215                 220

Pro Thr Thr Thr Phe Asp Arg Ala Ala Trp Glu Glu Ser Val Lys Arg
225             230                 235                 240

Pro Val Ala Arg Cys Thr Leu Asp Asn Gly Met Thr Asp Glu Ala Arg
                245                 250                 255

Gln Val Phe Leu Asp Lys His Asn Glu Tyr Arg Gln Leu Val Ala Arg
                260                 265                 270

Gly Glu Ala Lys Asn Lys Thr Gly Leu Ala Pro Pro Ala Ala Arg Met
            275                 280                 285

Leu Gln Met Arg Tyr Asp Cys Asp Leu Glu Ala His Val Met Glu His
            290                 295                 300

Val Lys Gln Cys Lys Gly Gly His Ser Ser Phe Asp Val Leu Lys Gly
305             310                 315                 320

Arg Gly Gln Asn Ile Trp Ala Ile Thr Val Pro Asn Leu Asp Lys Ala
                325                 330                 335

Asp Ala Ala Asn Arg Ser Val His Asp Trp Tyr Ile Glu Leu Thr Lys
            340                 345                 350

Tyr Gly Ile Thr Ala Asp Asn Lys Ile Ser Met Asp Asn Ala Ala Asn
            355                 360                 365

Thr Gly His Tyr Ser Gln Val Val Trp Gln Lys Ser Asn Arg Leu Gly
            370                 375                 380

Cys Ala Ala Val Ser Cys Pro Glu Gln Gly Lys Leu Phe Val Gly Cys
385             390                 395                 400

Glu Tyr Leu Pro Gly Gly Asn Thr Leu His His Leu Ile Tyr Asp Ile
                405                 410                 415

Gly Glu Pro Cys Lys Arg
            420

<210> SEQ ID NO 2
<211> LENGTH: 1266
<212> TYPE: DNA
<213> ORGANISM: Cooperia oncophora

<400> SEQUENCE: 2
gatgagatca gaaaagtctt ccttgacaag cacaatgagt accggtcact cgttgctaaa    60
ggacaggctc tgaatccaca gtttggcggg tctactccaa aggccgctag aatgctcaaa   120
gcgaggtacg attgcgatgt tgaagaagac atgacgaagt gggctcaagc gcagtgcacg   180

| | |
|---|---|
| tacgcaccat tcaaaagtag caaacgttac ggccggaaca catggggcat gggtgtccct | 240 |
| aactacaaca agacagcagc tgcagaatcg agtgtttacg actggttctt cgaactacgg | 300 |
| cgctatggtg ttcctcaaga taacgtgtat acaagagatg ttgactacag tgcttatcat | 360 |
| tacgctcaga tggtttggca agatagttac aaaattggat gtgtcgtggc atggtgtcca | 420 |
| agcatgacct gggtagcatg cggatacagt ccagcaggag ataatatcgg atccctaatt | 480 |
| tacgagcttg gagaaccgtg tacaaagaat gaagactgta atgcaccga ctgcacatgt | 540 |
| agtgaaggag aagctctttg tatacctcct ggaggaccga aacccgctac cactgcaagc | 600 |
| accacgacca agacaacgac cactacaaag cctacgacga cgacgacgga accttcgacc | 660 |
| actacggcga agccaacgac gaccttcgat agagctgcgt gggaggagtc ggtcaagagg | 720 |
| ccagtagcgc gttgcactct tgacaacgga atgacagacg aggccaggca ggttttcctt | 780 |
| gacaagcaca acgagtaccg gcaactagtt gcaagaggag aagctaaaaa caagacagga | 840 |
| ttggctccgc cggcagctag aatgctacaa atgaggtacg attgcgacct tgaggcacat | 900 |
| gttatggagc acgttaaaca gtgtaaaggc ggacattcat catttgatgt gcttaaaggt | 960 |
| aggggggcaga acatatgggc cataactgtc cctaacttgg acaaggctga tgctgcaaac | 1020 |
| cggagtgtcc atgactggta catcgaatta acgaaatatg gtataaccgc agataacaag | 1080 |
| atatcaatgg acaatgctgc aaacactggt cattactcgc aggtagtttg caaaagtcg | 1140 |
| aacagacttg gatgtgcagc ggtgtcctgt ccagaacaag gaaaactctt tgtaggttgc | 1200 |
| gaatatttac caggagggaa cacacttcac catctgattt acgatatcgg agagccatgc | 1260 |
| aaacgg | 1266 |

<210> SEQ ID NO 3
<211> LENGTH: 422
<212> TYPE: PRT
<213> ORGANISM: Cooperia oncophora

<400> SEQUENCE: 3

```
Asp Glu Ile Arg Lys Val Phe Leu Asp Lys His Asn Glu Tyr Arg Ser
1               5                   10                  15

Leu Val Ala Lys Gly Gln Ala Pro Asn Pro Gln Phe Gly Gly Ser Thr
            20                  25                  30

Pro Lys Ala Ala Arg Met Leu Lys Ala Met Tyr Asp Cys Asp Val Glu
        35                  40                  45

Glu Asp Met Thr Lys Trp Ala Gln Ala Gln Cys Thr Tyr Ala Pro Phe
    50                  55                  60

Lys Ser Ser Lys His Tyr Gly Arg Asn Thr Trp Gly Met Gly Val Pro
65                  70                  75                  80

Asn Tyr Asn Lys Thr Ala Ala Ala Glu Ser Ser Val Tyr Asp Trp Phe
                85                  90                  95

Ser Glu Leu Arg Arg Tyr Gly Val Pro Gln Asp Asn Val Tyr Thr Arg
            100                 105                 110

Asp Val Asp Tyr Ser Ala Tyr Gln Tyr Ala Gln Met Val Trp Gln Asp
        115                 120                 125

Ser Tyr Lys Ile Gly Cys Val Ala Trp Cys Pro Ser Val Thr Trp
    130                 135                 140

Val Ala Cys Gly Tyr Ser Pro Ala Gly Asp Asn Ile Gly Ser Leu Ile
145                 150                 155                 160

Tyr Glu Leu Gly Glu Pro Cys Thr Lys Asn Glu Asp Cys Lys Cys Thr
                165                 170                 175
```

Asp Cys Thr Cys Ser Glu Gly Glu Ala Leu Cys Ile Pro Pro Gly Gly
            180                 185                 190

Pro Lys Pro Ala Thr Thr Ala Ser Thr Thr Lys Thr Thr Thr
        195                 200                 205

Thr Lys Pro Thr Thr Thr Thr Lys Leu Ser Thr Thr Thr Ala Lys
        210                 215                 220

Pro Thr Thr Thr Phe Asp Arg Ala Ala Trp Glu Ser Val Lys Arg
225                 230                 235                 240

Pro Val Ala Arg Cys Thr Leu Asp Asn Gly Met Thr Asp Glu Ala Arg
                245                 250                 255

Gln Val Phe Leu Asp Lys His Asn Glu Tyr Arg Gln Leu Val Ala Arg
            260                 265                 270

Gly Glu Ala Lys Asn Lys Thr Gly Leu Ala Pro Pro Ala Ala Arg Met
        275                 280                 285

Leu Gln Met Arg Tyr Asp Cys Asp Leu Glu Ala His Val Met Glu His
        290                 295                 300

Val Lys Gln Cys Lys Gly Gly His Ser Ser Phe Asp Val Leu Lys Gly
305                 310                 315                 320

Arg Gly Gln Asn Ile Trp Ala Ile Thr Val Pro Asn Leu Asp Lys Ala
                325                 330                 335

Asp Ala Ala Asn Arg Ser Val His Asp Trp Tyr Ile Glu Leu Thr Lys
            340                 345                 350

Tyr Gly Ile Thr Ala Asp Asn Lys Ile Ser Met Asp Asn Ala Ala Asn
        355                 360                 365

Thr Gly His Tyr Ser Gln Val Val Trp Gln Lys Ser Asn Arg Leu Gly
        370                 375                 380

Cys Ala Ala Val Ser Cys Pro Glu Gln Gly Lys Leu Phe Val Gly Cys
385                 390                 395                 400

Glu Tyr Leu Pro Gly Gly Asn Thr Leu His His Leu Ile Tyr Asp Ile
                405                 410                 415

Gly Glu Pro Cys Lys Arg
            420

<210> SEQ ID NO 4
<211> LENGTH: 1266
<212> TYPE: DNA
<213> ORGANISM: Cooperia oncophora

<400> SEQUENCE: 4
gatgagatca ggaaagtctt ccttgacaag cacaatgagt atcggtcact cgttgctaaa      60
ggacaggctc cgaatccaca gtttggcgga tctactccaa aggccgctag aatgctcaaa     120
gcgatgtacg attgcgatgt tgaagaagac atgacgaagt gggctcaagc gcagtgcacg     180
tacgcaccat tcaaaagtag caaacattac ggccggaaca catggggcat gggtgtccct     240
aactacaaca agacagcagc tgcagaatcg agtgtttacg actggttctc gaactacgg      300 cgctatggtg ttcctcaaga taacgtgtat acaagagatg ttgactacag tgcttatcaa     360
tacgctcaga tggtttggca agacagttac aaaattggat gtgtcgtggc atggtgtcca     420
agcgtgacct gggtagcgtg cggatacagt ccagcaggag ataatatcgg atccctaatt     480
tacgagcttg gagaaccgtg tacgaagaat gaagactgta atgcaccga ctgcacatgt     540 agtgaaggag aagctctttg tatacctcct ggaggaccaa acccgctac cactgcaagc     600 accacaacca agacaacgac cactacaaag cctacgacga cgacgacgaa actttcgacc     660
actacggcga agccaacgac gaccttcgat agagctgcgt gggaggagtc ggtcaagagg     720

```
ccagtagcgc gttgcactct tgacaacgga atgacagacg aggccaggca ggttttcctt    780
gacaagcaca acgagtaccg acaactagtt gcaagaggag aagctaaaaa caagacagga    840
ttggctccgc cggcagctag aatgctacaa atgaggtacg attgcgacct tgaggcacat    900
gttatggagc acgttaaaca atgtaaaggc ggacattcat catttgatgt gcttaaaggt    960 aggggcaga acatatgggc cataactgtc cctaacttgg acaaggctga tgctgcaaac    1020
cggagtgtcc atgactggta catcgaatta acgaaatatg gtataactgc agataacaag    1080
atatcaatgg acaatgctgc aaacactggt cattactcgc aggtagtttg gcaaaagtcg    1140
aacagacttg gatgtgcagc ggtgtcctgt ccagaacaag gaaaactctt tgtaggttgc    1200
gaatatttac caggagggaa cacacttcac catctgattt acgatatcgg agagccatgc    1260
aaacgg                                                               1266

<210> SEQ ID NO 5
<211> LENGTH: 422
<212> TYPE: PRT
<213> ORGANISM: Cooperia oncophora

<400> SEQUENCE: 5

Asp Glu Ile Arg Lys Val Phe Leu Asp Lys His Asn Glu Tyr Arg Ser
1               5                   10                  15

Leu Val Ala Lys Gly Gln Ala Pro Asn Pro Gln Phe Gly Gly Ser Thr
            20                  25                  30

Pro Lys Ala Ala Arg Met Leu Lys Ala Arg Tyr Asp Cys Asp Val Glu
        35                  40                  45

Glu Asp Met Thr Lys Trp Ala Gln Ala Gln Cys Thr Tyr Ala Pro Phe
    50                  55                  60

Lys Ser Ser Lys Arg Tyr Gly Arg Asn Thr Trp Gly Met Gly Val Pro
65                  70                  75                  80

Asn Tyr Asn Lys Ile Ala Ala Ala Glu Ser Ser Val Asp Asp Trp Phe
                85                  90                  95

Phe Glu Leu Arg Arg Tyr Gly Val Pro Gln Asp Asn Val Tyr Thr Arg
            100                 105                 110

Asp Val Asp Tyr Ser Ala Tyr His Tyr Ala Gln Met Val Trp Gln Asp
        115                 120                 125

Ser Tyr Lys Ile Gly Cys Val Val Ala Trp Cys Pro Ser Met Thr Trp
    130                 135                 140

Val Ala Cys Gly Tyr Ser Pro Ala Gly Asp Asn Ile Gly Ser Leu Ile
145                 150                 155                 160

Tyr Glu Leu Gly Glu Pro Cys Thr Lys Asn Glu Asp Cys Lys Cys Thr
                165                 170                 175

Asp Cys Thr Cys Ser Glu Gly Glu Ala Leu Cys Ile Pro Pro Gly Glu
            180                 185                 190

Pro Lys Pro Ala Thr Thr Ala Ser Thr Thr Lys Thr Thr Thr Thr
        195                 200                 205

Thr Glu Pro Thr Thr Thr Thr Thr Glu Pro Ser Thr Thr Thr Ala Lys
    210                 215                 220

Pro Thr Thr Thr Phe Asp Arg Ala Ala Trp Glu Glu Ser Val Lys Arg
225                 230                 235                 240

Pro Val Ala Arg Cys Thr Leu Asp Asn Gly Met Thr Asp Glu Ala Arg
                245                 250                 255

Gln Val Phe Leu Asp Lys His Asn Glu Tyr Arg Gln Leu Val Ala Arg
            260                 265                 270
```

```
Gly Glu Ala Lys Asn Lys Thr Gly Leu Ala Pro Pro Ala Ala Arg Met
            275                 280                 285

Leu Gln Met Arg Tyr Asp Cys Asp Leu Glu Ala His Val Met Glu His
        290                 295                 300

Val Lys Gln Cys Lys Gly Gly His Ser Ser Phe Asp Val Leu Lys Gly
305                 310                 315                 320

Arg Gly Gln Asn Ile Trp Ala Ile Thr Val Pro Asn Leu Asp Lys Ala
                325                 330                 335

Asp Ala Ala Asn Arg Ser Val His Asp Trp Tyr Ile Glu Leu Thr Lys
            340                 345                 350

Tyr Gly Ile Thr Ala Asp Asn Lys Ile Ser Met Asp Asn Ala Ala Asn
        355                 360                 365

Thr Gly His Tyr Ser Gln Val Val Trp Gln Lys Ser Asn Arg Leu Gly
    370                 375                 380

Cys Ala Ala Val Ser Cys Pro Glu Gln Gly Lys Leu Phe Val Gly Cys
385                 390                 395                 400

Glu Tyr Leu Pro Gly Gly Asn Thr Leu His His Leu Ile Tyr Asp Ile
                405                 410                 415

Gly Glu Pro Cys Lys Arg
            420
```

<210> SEQ ID NO 6
<211> LENGTH: 1266
<212> TYPE: DNA
<213> ORGANISM: Cooperia oncophora

<400> SEQUENCE: 6

```
gatgagatca gaaaagtctt ccttgacaag cacaatgagt atcggtcact cgttgctaaa      60
ggacaggctc cgaatccaca gtttggcggg tctactccaa aggccgctag aatgctcaaa     120
gcgaggtacg attgcgatgt tgaagaagac atgacgaagt gggctcaagc gcagtgcacg     180
tacgcaccat tcaaaagtag caaacgttac ggccggaaca catggggaat gggtgtccct     240
aactacaaca agatagcagc tgcagaatcg agtgttgacg actggttctt cgaactacgg     300
cgctatggtg ttcctcaaga taacgtgtat acaagagatg ttgactacag tgcttatcat     360
tacgctcaga tggtttggca agacagttac aaaattggat gtgtcgtggc atggtgtcca     420
agcatgacct gggtagcgtg cggatacagt ccagcaggag ataatatcgg atccctaatt     480
tacgagcttg gagaaccgtg tacaaagaat gaagactgta aatgcaccga ctgcacatgt     540
agtgaaggag aagctctttg tatacctcct ggagaaccga acccgctac cactgcaagc      600 accacgacca agacaacgac cactacagag cctacgacaa cgacgacgga accgtcgacc     660
actacggcga agccaacgac gaccttcgat agagctgcgt gggaggagtc ggtcaagagg     720
ccagtagcgc gttgcactct tgacaacgga atgacagacg aggccaggca ggtttccctc     780
gacaagcaca acgagtaccg gcaactagtt gcaagaggag aagctaaaaa caagacagga     840
ttggctccgc cggcagctag aatgctacaa atgaggtacg attgcgacct tgaggcacat     900
gttatggagc acgttaaaca atgtaaaggc ggacattcat catttgatgt gcttaaaggt     960 aggggggcaga acatatgggc cataactgtc cctaacttgg acaaggctga tgctgcaaac    1020
cggagtgtcc atgactggta catcgaatta acgaaatatg gtataactgc agataacaag    1080
atatcaatgg acaatgctgc aaacactggt cattactcgc aggtagtttg caaaagtcg     1140 aacagacttg gatgtgcagc ggtgtcctgt ccagaacaag gaaaactctt tgtaggttgc    1200
```

-continued

```
gaatatttac caggagggaa cacacttcac catctgattt acgatatcgg agagccatgc    1260
aaacgg                                                              1266

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
atgyaacagk aytgggtgag g                                               21

<210> SEQ ID NO 8
<211> LENGTH: 23
<212> TYPE: DNA
<213> ORGANISM: Artificial sequence
<220> FEATURE:
<223> OTHER INFORMATION: Primer

<400> SEQUENCE: 8
atacacatgg ayaaytgtgt gct                                             23

<210> SEQ ID NO 9
<211> LENGTH: 10
<212> TYPE: PRT
<213> ORGANISM: Cooperia oncophora

<400> SEQUENCE: 9

Leu Arg Trp Asn Cys Thr Leu Glu Ala Lys
1               5                   10

<210> SEQ ID NO 10
<211> LENGTH: 8
<212> TYPE: PRT
<213> ORGANISM: Cooperia oncophora

<400> SEQUENCE: 10

Trp Asn Cys Thr Leu Glu Ala Lys
1               5

<210> SEQ ID NO 11
<211> LENGTH: 10
<212> TYPE: PRT
<213> ORGANISM: Cooperia oncophora

<400> SEQUENCE: 11

Trp Asn Cys Thr Leu Glu Ala Lys Ala Arg
1               5                   10

<210> SEQ ID NO 12
<211> LENGTH: 27
<212> TYPE: DNA
<213> ORGANISM: Cooperia oncophora

<400> SEQUENCE: 12
ctttgctcgc ttgataatgg aatgaca                                         27

<210> SEQ ID NO 13
<211> LENGTH: 66
<212> TYPE: DNA
<213> ORGANISM: Cooperia oncophora
```

<400> SEQUENCE: 13
gatgaagatt gtaagtgcag ctcctgcaga tgcagcacac aattatccat gtgtatcaac    60
cctaac    66

<210> SEQ ID NO 14
<211> LENGTH: 9
<212> TYPE: PRT
<213> ORGANISM: Cooperia oncophora

<400> SEQUENCE: 14

Leu Cys Ser Leu Asp Asn Gly Met Thr
1               5

<210> SEQ ID NO 15
<211> LENGTH: 22
<212> TYPE: PRT
<213> ORGANISM: Cooperia oncophora

<400> SEQUENCE: 15

Asp Glu Asp Cys Lys Cys Ser Ser Cys Arg Cys Ser Thr Gln Leu Ser
1               5                   10                  15

Met Cys Ile Asn Pro Asn
            20

<210> SEQ ID NO 16
<211> LENGTH: 453
<212> TYPE: PRT
<213> ORGANISM: Cooperia oncophora

<400> SEQUENCE: 16

Leu Cys Ser Leu Asp Asn Gly Met Thr Asp Glu Ile Arg Lys Val Phe
1               5                   10                  15

Leu Asp Lys His Asn Glu Tyr Arg Ser Leu Val Ala Lys Gly Gln Ala
            20                  25                  30

Leu Asn Pro Gln Phe Gly Gly Ser Thr Pro Lys Ala Ala Arg Met Leu
        35                  40                  45

Lys Ala Arg Tyr Asp Cys Asp Val Glu Asp Met Thr Lys Trp Ala
    50                  55                  60

Gln Ala Gln Cys Thr Tyr Ala Pro Phe Lys Ser Ser Lys Arg Tyr Gly
65                  70                  75                  80

Arg Asn Thr Trp Gly Met Gly Val Pro Asn Tyr Asn Lys Thr Ala Ala
                85                  90                  95

Ala Glu Ser Ser Val Tyr Asp Trp Phe Phe Glu Leu Arg Arg Tyr Gly
            100                 105                 110

Val Pro Gln Asp Asn Val Tyr Thr Arg Asp Val Asp Tyr Ser Ala Tyr
        115                 120                 125

His Tyr Ala Gln Met Val Trp Gln Asp Ser Tyr Lys Ile Gly Cys Val
    130                 135                 140

Val Ala Trp Cys Pro Ser Met Thr Trp Val Ala Cys Gly Tyr Ser Pro
145                 150                 155                 160

Ala Gly Asp Asn Ile Gly Ser Leu Ile Tyr Glu Leu Gly Glu Pro Cys
                165                 170                 175

Thr Lys Asn Glu Asp Cys Lys Cys Thr Asp Cys Thr Cys Ser Glu Gly
            180                 185                 190

Glu Ala Leu Cys Ile Pro Pro Gly Gly Pro Lys Pro Ala Thr Thr Ala
        195                 200                 205

```
Ser Thr Thr Thr Lys Thr Thr Thr Thr Lys Pro Thr Thr Thr Thr
    210                 215                 220

Thr Glu Pro Ser Thr Thr Thr Ala Lys Pro Thr Thr Thr Phe Asp Arg
225                 230                 235                 240

Ala Ala Trp Glu Glu Ser Val Lys Arg Pro Val Ala Arg Cys Thr Leu
                245                 250                 255

Asp Asn Gly Met Thr Asp Glu Ala Arg Gln Val Phe Leu Asp Lys His
            260                 265                 270

Asn Glu Tyr Arg Gln Leu Val Ala Arg Gly Glu Ala Lys Asn Lys Thr
        275                 280                 285

Gly Leu Ala Pro Pro Ala Ala Arg Met Leu Gln Met Arg Tyr Asp Cys
    290                 295                 300

Asp Leu Glu Ala His Val Met Glu His Val Lys Gln Cys Lys Gly Gly
305                 310                 315                 320

His Ser Ser Phe Asp Val Leu Lys Gly Arg Gly Gln Asn Ile Trp Ala
                325                 330                 335

Ile Thr Val Pro Asn Leu Asp Lys Ala Asp Ala Ala Asn Arg Ser Val
            340                 345                 350

His Asp Trp Tyr Ile Glu Leu Thr Lys Tyr Gly Ile Thr Ala Asp Asn
        355                 360                 365

Lys Ile Ser Met Asp Asn Ala Ala Asn Thr Gly His Tyr Ser Gln Val
    370                 375                 380

Val Trp Gln Lys Ser Asn Arg Leu Gly Cys Ala Ala Val Ser Cys Pro
385                 390                 395                 400

Glu Gln Gly Lys Leu Phe Val Gly Cys Glu Tyr Leu Pro Gly Gly Asn
                405                 410                 415

Thr Leu His His Leu Ile Tyr Asp Ile Gly Glu Pro Cys Lys Arg Asp
            420                 425                 430

Glu Asp Cys Lys Cys Ser Ser Cys Arg Cys Ser Thr Gln Leu Ser Met
        435                 440                 445

Cys Ile Asn Pro Asn
    450

<210> SEQ ID NO 17
<211> LENGTH: 453
<212> TYPE: PRT
<213> ORGANISM: Cooperia oncophora

<400> SEQUENCE: 17

Leu Cys Ser Leu Asp Asn Gly Met Thr Asp Glu Ile Arg Lys Val Phe
1               5                   10                  15

Leu Asp Lys His Asn Glu Tyr Arg Ser Leu Val Ala Lys Gly Gln Ala
            20                  25                  30

Pro Asn Pro Gln Phe Gly Gly Ser Thr Pro Lys Ala Ala Arg Met Leu
        35                  40                  45

Lys Ala Met Tyr Asp Cys Asp Val Glu Glu Asp Met Thr Lys Trp Ala
    50                  55                  60

Gln Ala Gln Cys Thr Tyr Ala Pro Phe Lys Ser Ser Lys His Tyr Gly
65                  70                  75                  80

Arg Asn Thr Trp Gly Met Gly Val Pro Asn Tyr Asn Lys Thr Ala Ala
                85                  90                  95

Ala Glu Ser Ser Val Tyr Asp Trp Phe Ser Glu Leu Arg Arg Tyr Gly
            100                 105                 110

Val Pro Gln Asp Asn Val Tyr Thr Arg Asp Val Asp Tyr Ser Ala Tyr
        115                 120                 125
```

Gln Tyr Ala Gln Met Val Trp Gln Asp Ser Tyr Lys Ile Gly Cys Val
130                 135                 140

Val Ala Trp Cys Pro Ser Val Thr Trp Val Ala Cys Gly Tyr Ser Pro
145                 150                 155                 160

Ala Gly Asp Asn Ile Gly Ser Leu Ile Tyr Glu Leu Gly Glu Pro Cys
                165                 170                 175

Thr Lys Asn Glu Asp Cys Lys Cys Thr Asp Cys Thr Cys Ser Glu Gly
                180                 185                 190

Glu Ala Leu Cys Ile Pro Pro Gly Gly Pro Lys Pro Ala Thr Thr Ala
                195                 200                 205

Ser Thr Thr Thr Lys Thr Thr Thr Thr Thr Lys Pro Thr Thr Thr Thr
210                 215                 220

Thr Lys Leu Ser Thr Thr Thr Ala Lys Pro Thr Thr Thr Phe Asp Arg
225                 230                 235                 240

Ala Ala Trp Glu Glu Ser Val Lys Arg Pro Val Ala Arg Cys Thr Leu
                245                 250                 255

Asp Asn Gly Met Thr Asp Glu Ala Arg Gln Val Phe Leu Asp Lys His
                260                 265                 270

Asn Glu Tyr Arg Gln Leu Val Ala Arg Gly Glu Ala Lys Asn Lys Thr
                275                 280                 285

Gly Leu Ala Pro Pro Ala Ala Arg Met Leu Gln Met Arg Tyr Asp Cys
290                 295                 300

Asp Leu Glu Ala His Val Met Glu His Val Lys Gln Cys Lys Gly Gly
305                 310                 315                 320

His Ser Ser Phe Asp Val Leu Lys Gly Arg Gly Gln Asn Ile Trp Ala
                325                 330                 335

Ile Thr Val Pro Asn Leu Asp Lys Ala Asp Ala Ala Asn Arg Ser Val
                340                 345                 350

His Asp Trp Tyr Ile Glu Leu Thr Lys Tyr Gly Ile Thr Ala Asp Asn
                355                 360                 365

Lys Ile Ser Met Asp Asn Ala Ala Asn Thr Gly His Tyr Ser Gln Val
                370                 375                 380

Val Trp Gln Lys Ser Asn Arg Leu Gly Cys Ala Ala Val Ser Cys Pro
385                 390                 395                 400

Glu Gln Gly Lys Leu Phe Val Gly Cys Glu Tyr Leu Pro Gly Gly Asn
                405                 410                 415

Thr Leu His His Leu Ile Tyr Asp Ile Gly Glu Pro Cys Lys Arg Asp
                420                 425                 430

Glu Asp Cys Lys Cys Ser Ser Cys Arg Cys Ser Thr Gln Leu Ser Met
                435                 440                 445

Cys Ile Asn Pro Asn
            450

<210> SEQ ID NO 18
<211> LENGTH: 453
<212> TYPE: PRT
<213> ORGANISM: Cooperia oncophora

<400> SEQUENCE: 18

Leu Cys Ser Leu Asp Asn Gly Met Thr Asp Glu Ile Arg Lys Val Phe
1               5                   10                  15

Leu Asp Lys His Asn Glu Tyr Arg Ser Leu Val Ala Lys Gly Gln Ala
                20                  25                  30

Pro Asn Pro Gln Phe Gly Gly Ser Thr Pro Lys Ala Ala Arg Met Leu
                35                  40                  45

-continued

```
Lys Ala Arg Tyr Asp Cys Asp Val Glu Glu Asp Met Thr Lys Trp Ala
    50                  55                  60
Gln Ala Gln Cys Thr Tyr Ala Pro Phe Lys Ser Ser Lys Arg Tyr Gly
65                  70                  75                  80
Arg Asn Thr Trp Gly Met Gly Val Pro Asn Tyr Asn Lys Ile Ala Ala
                85                  90                  95
Ala Glu Ser Ser Val Asp Asp Trp Phe Phe Glu Leu Arg Arg Tyr Gly
                100                 105                 110
Val Pro Gln Asp Asn Val Tyr Thr Arg Asp Val Asp Tyr Ser Ala Tyr
                115                 120                 125
His Tyr Ala Gln Met Val Trp Gln Asp Ser Tyr Lys Ile Gly Cys Val
    130                 135                 140
Val Ala Trp Cys Pro Ser Met Thr Trp Val Ala Cys Gly Tyr Ser Pro
145                 150                 155                 160
Ala Gly Asp Asn Ile Gly Ser Leu Ile Tyr Glu Leu Gly Glu Pro Cys
                165                 170                 175
Thr Lys Asn Glu Asp Cys Lys Cys Thr Asp Cys Thr Cys Ser Glu Gly
                180                 185                 190
Glu Ala Leu Cys Ile Pro Pro Gly Glu Pro Lys Pro Ala Thr Thr Ala
            195                 200                 205
Ser Thr Thr Thr Lys Thr Thr Thr Thr Thr Glu Pro Thr Thr Thr Thr
    210                 215                 220
Thr Glu Pro Ser Thr Thr Thr Ala Lys Pro Thr Thr Thr Phe Asp Arg
225                 230                 235                 240
Ala Ala Trp Glu Glu Ser Val Lys Arg Pro Val Ala Arg Cys Thr Leu
                245                 250                 255
Asp Asn Gly Met Thr Asp Glu Ala Arg Gln Val Phe Leu Asp Lys His
                260                 265                 270
Asn Glu Tyr Arg Gln Leu Val Ala Arg Gly Glu Ala Lys Asn Lys Thr
            275                 280                 285
Gly Leu Ala Pro Pro Ala Ala Arg Met Leu Gln Met Arg Tyr Asp Cys
    290                 295                 300
Asp Leu Glu Ala His Val Met Glu His Val Lys Gln Cys Lys Gly Gly
305                 310                 315                 320
His Ser Ser Phe Asp Val Leu Lys Gly Arg Gly Gln Asn Ile Trp Ala
                325                 330                 335
Ile Thr Val Pro Asn Leu Asp Lys Ala Asp Ala Ala Asn Arg Ser Val
                340                 345                 350
His Asp Trp Tyr Ile Glu Leu Thr Lys Tyr Gly Ile Thr Ala Asp Asn
            355                 360                 365
Lys Ile Ser Met Asp Asn Ala Ala Asn Thr Gly His Tyr Ser Gln Val
    370                 375                 380
Val Trp Gln Lys Ser Asn Arg Leu Gly Cys Ala Ala Val Ser Cys Pro
385                 390                 395                 400
Glu Gln Gly Lys Leu Phe Val Gly Cys Glu Tyr Leu Pro Gly Gly Asn
                405                 410                 415
Thr Leu His His Leu Ile Tyr Asp Ile Gly Glu Pro Cys Lys Arg Asp
            420                 425                 430
Glu Asp Cys Lys Cys Ser Ser Cys Arg Cys Ser Thr Gln Leu Ser Met
    435                 440                 445
Cys Ile Asn Pro Asn
    450
```

<210> SEQ ID NO 19
<211> LENGTH: 1359
<212> TYPE: DNA
<213> ORGANISM: Cooperia oncophora

<400> SEQUENCE: 19

| | | | | | |
|---|---|---|---|---|---|
| ctttgctcgc | ttgataatgg | aatgacagat | gagatcagaa | aagtcttcct | tgacaagcac | 60 |
| aatgagtacc | ggtcactcgt | tgctaaagga | caggctctga | atccacagtt | tggcgggtct | 120 |
| actccaaagg | ccgctagaat | gctcaaagcg | aggtacgatt | gcgatgttga | agaagacatg | 180 |
| acgaagtggg | ctcaagcgca | gtgcacgtac | gcaccattca | aaagtagcaa | acgttacggc | 240 |
| cggaacacat | gggcatggg | tgtccctaac | tacaacaaga | cagcagctgc | agaatcgagt | 300 |
| gtttacgact | ggttcttcga | actacggcgc | tatggtgttc | ctcaagataa | cgtgtataca | 360 |
| agagatgttg | actacagtgc | ttatcattac | gctcagatgg | tttggcaaga | tagttacaaa | 420 |
| attggatgtg | tcgtggcatg | gtgtccaagc | atgacctggg | tagcatgcgg | atacagtcca | 480 |
| gcaggagata | atatcggatc | cctaatttac | gagcttggag | aaccgtgtac | aaagaatgaa | 540 |
| gactgtaaat | gcaccgactg | cacatgtagt | gaaggagaag | ctctttgtat | acctcctgga | 600 |
| ggaccgaaac | ccgctaccac | tgcaagcacc | acgaccaaga | caacgaccac | tacaaagcct | 660 |
| acgacgacga | cgacggaacc | ttcgaccact | acggcgaagc | caacgacgac | cttcgataga | 720 |
| gctgcgtggg | aggagtcggt | caagaggcca | gtagcgcgtt | gcactcttga | caacggaatg | 780 |
| acagacgagg | ccaggcaggt | tttccttgac | aagcacaacg | agtaccggca | actagttgca | 840 |
| agaggagaag | ctaaaaacaa | gacaggattg | gctccgccgg | cagctagaat | gctacaaatg | 900 |
| aggtacgatt | gcgaccttga | ggcacatgtt | atggagcacg | ttaaacagtg | taaaggcgga | 960 |
| cattcatcat | ttgatgtgct | taaaggtagg | gggcagaaca | tatgggccat | aactgtccct | 1020 |
| aacttggaca | aggctgatgc | tgcaaaccgg | agtgtccatg | actggtacat | cgaattaacg | 1080 |
| aaatatggta | taaccgcaga | taacaagata | tcaatggaca | atgctgcaaa | cactggtcat | 1140 |
| tactcgcagg | tagtttggca | aaagtcgaac | agacttggat | gtgcagcggt | gtcctgtcca | 1200 |
| gaacaaggaa | aactctttgt | aggttgcgaa | tatttaccag | gagggaacac | acttcaccat | 1260 |
| ctgatttacg | atatcggaga | gccatgcaaa | cgggatgaag | attgtaagtg | cagctcctgc | 1320 |
| agatgcagca | cacaattatc | catgtgtatc | aaccctaac | | | 1359 |

<210> SEQ ID NO 20
<211> LENGTH: 1359
<212> TYPE: DNA
<213> ORGANISM: Cooperia oncophora

<400> SEQUENCE: 20

| | | | | | |
|---|---|---|---|---|---|
| ctttgctcgc | tggataatgg | aatgacagat | gagatcagga | aagtcttcct | tgacaagcac | 60 |
| aatgagtatc | ggtcactcgt | tgctaaagga | caggctccga | atccacagtt | tggcggatct | 120 |
| actccaaagg | ccgctagaat | gctcaaagcg | atgtacgatt | gcgatgttga | agaagacatg | 180 |
| acgaagtggg | ctcaagcgca | gtgcacgtac | gcaccattca | aaagtagcaa | acattacggc | 240 |
| cggaacacat | gggcatggg | tgtccctaac | tacaacaaga | cagcagctgc | agaatcgagt | 300 |
| gtttacgact | ggttctccga | actacggcgc | tatggtgttc | ctcaagataa | cgtgtataca | 360 |
| agagatgttg | actacagtgc | ttatcaatac | gctcagatgg | tttggcaaga | cagttacaaa | 420 |
| attggatgtg | tcgtggcatg | gtgtccaagc | gtgacctggg | tagcgtgcgg | atacagtcca | 480 |
| gcaggagata | atatcggatc | cctaatttac | gagcttggag | aaccgtgtac | gaagaatgaa | 540 |

```
gactgtaaat gcaccgactg cacatgtagt gaaggagaag ctctttgtat acctcctgga    600
ggaccaaaac ccgctaccac tgcaagcacc acaaccaaga caacgaccac tacaaagcct    660
acgacgacga cgacgaaact ttcgaccact acggcgaagc caacgacgac cttcgataga    720
gctgcgtggg aggagtcggt caagaggcca gtagcgcgtt gcactcttga caacggaatg    780
acagacgagg ccaggcaggt tttccttgac aagcacaacg agtaccgaca actagttgca    840
agaggagaag ctaaaaacaa gacaggattg gctccgccgg cagctagaat gctacaaatg    900
aggtacgatt gcgaccttga ggcacatgtt atggagcacg ttaaacaatg taaaggcgga    960
cattcatcat ttgatgtgct taaaggtagg gggcagaaca tatgggccat aactgtccct   1020
aacttggaca aggctgatgc tgcaaaccgg agtgtccatg actggtacat cgaattaacg   1080
aaatatggta taactgcaga taacaagata tcaatggaca atgctgcaaa cactggtcat   1140
tactcgcagg tagtttggca aaagtcgaac agacttggat gtgcagcggt gtcctgtcca   1200
gaacaaggaa aactctttgt aggttgcgaa tatttaccag gagggaacac acttcaccat   1260
ctgatttacg atatcggaga gccatgcaaa cgggatgaag attgtaagtg cagctcctgc   1320
agatgcagca cacaattatc catgtgtatc aaccctaac                           1359

<210> SEQ ID NO 21
<211> LENGTH: 1359
<212> TYPE: DNA
<213> ORGANISM: Cooperia oncophora

<400> SEQUENCE: 21
ctttgctcgc tggataatgg aatgacagat gagatcagaa aagtcttcct tgacaagcac     60
aatgagtatc ggtcactcgt tgctaaagga caggctccga atccacagtt tggcgggtct    120
actccaaagg ccgctagaat gctcaaagcg aggtacgatt gcgatgttga agaagacatg    180
acgaagtggg ctcaagcgca gtgcacgtac gcaccattca aaagtagcaa acgttacggc    240
cggaacacat ggggaatggg tgtccctaac tacaacaaga tagcagctgc agaatcgagt    300
gttgacgact ggttcttcga actacggcgc tatggtgttc ctcaagataa cgtgtataca    360
agagatgttg actacagtgc ttatcattac gctcagatgg tttggcaaga cagttacaaa    420
attggatgtg tcgtggcatg gtgtccaagc atgacctggg tagcgtgcgg atacagtcca    480
gcaggagata atatcggatc cctaatttac gagcttggag aaccgtgtac aaagaatgaa    540
gactgtaaat gcaccgactg cacatgtagt gaaggagaag ctctttgtat acctcctgga    600
gaaccgaaac ccgctaccac tgcaagcacc acgaccaaga caacgaccac tacagagcct    660 acgcaacga cgacggaacc gtcgaccact acggcgaagc caacgacgac cttcgataga    720
gctgcgtggg aggagtcggt caagaggcca gtagcgcgtt gcactcttga caacggaatg    780
acagacgagg ccaggcaggt ttccctcgac aagcacaacg agtaccggca actagttgca    840
agaggagaag ctaaaaacaa gacaggattg gctccgccgg cagctagaat gctacaaatg    900
aggtacgatt gcgaccttga ggcacatgtt atggagcacg ttaaacaatg taaaggcgga    960
cattcatcat ttgatgtgct taaaggtagg gggcagaaca tatgggccat aactgtccct   1020
aacttggaca aggctgatgc tgcaaaccgg agtgtccatg actggtacat cgaattaacg   1080
aaatatggta taactgcaga taacaagata tcaatggaca atgctgcaaa cactggtcat   1140
tactcgcagg tagtttggca aaagtcgaac agacttggat gtgcagcggt gtcctgtcca   1200
gaacaaggaa aactctttgt aggttgcgaa tatttaccag gagggaacac acttcaccat   1260
```

```
ctgatttacg atatcggaga gccatgcaaa cgggatgaag attgtaagtg cagctcctgc    1320
agatgcagca cacaattgtc catgtgtatc aaccctaac                           1359
```

COOPERIA VACCINE

CROSS-REFERENCE TO RELATED APPLICATIONS

This application is filed under 35 U.S.C. § 111 as a continuation of U.S. application Ser. No. 14/434,111 filed Apr. 8, 2015, which is a U.S. National Stage Entry of International Application No. PCT/EP2013/070903, filed Oct. 8, 2013, which designates the United States and claims priority to European Patent Office Application No. 12187773.2, filed Oct. 9, 2012, the contents of which are hereby incorporated by reference in their entirety.

FIELD OF THE INVENTION

The present invention relates to nucleotide sequences encoding *Cooperia* antigens, as well as to recombinant DNA molecules containing such nucleotide sequences and host cells expressing these nucleotide sequences. The invention further relates to *Cooperia* proteins, to methods for the production of the proteins, nucleotide sequences, recombinant DNA molecules and hosts.

Furthermore, the invention relates to vaccines which induce protective immunity against infection by parasitic nematodes such as species of the genus *Cooperia* and to methods for preparing such a vaccine.

BACKGROUND TO THE INVENTION

Nematodes, which are unsegmented roundworms with elongated, fusiform, or saclike bodies covered with cuticle, are virtually ubiquitous in nature, inhabiting soil, water and plants, and are importantly involved in a wide range of animal and plant parasitic diseases. Infections with gastro-intestinal nematodes are a major constraint on ruminant (cattle, sheep, goats, etc.) welfare and production worldwide. Infections with these parasites can lead to severe disease (diarrhea or anemia are typical symptoms). Among the economically important effects on livestock are reduction in milk, meat and wool production, weight gain and occasional death.

Important trichostrongylid parasites in cattle (bovine) are *Cooperia oncophora, C. punctata, C. pectinata, C. curticei* and *Ostertagia ostertagi*. In small ruminants, e.g. sheep and goats, infections with Haemonchus contortus and Teladorsagia circumcincta are the most important. Although being regarded as a mild pathogen, the helminth *Cooperia oncophora* is one of the most common intestinal parasitic nematodes in cattle in temperate climate regions worldwide (1) and as such carries a substantial economical footprint as it holds a profound share in production losses (2, 3). A recent study demonstrated that helminth infections increase United States beef production costs by nearly $190 per head according to 2005 market prices (4). Analogous to the use of antibiotics in humans, anthelmintics have long been the method of choice to treat and prevent parasite infections in a reasonably efficient and low-cost manner. For use in cattle, three major classes of anthelmintics are currently available, i.e. imidazothiazoles, benzimidazoles and macrocyclic lactones, the latter being the most frequently used in *Cooperia oncophora* treatments. However, the downside to this medal has gradually become apparent during the last decade as numerous reports of developing anthelmintic resistance have surfaced throughout the world (5-9). In addition, there is a concern regarding drug residues in meat and the environment. More effective avenues in controlling helminth infections are therefore highly necessary, one of which may involve the development and administration of prophylactic vaccines.

Since the issues surrounding anthelmintic resistance are observed for a multitude of helminths, numerous research groups have invested in the development of recombinant vaccines for e.g. *Ancylostoma caninum* (10), *Onchorcerca volvulus* (11-14), *Ascaris suum* (15-17), *Haemonchus contortus* (18, 19), *Necator americanus* (20), and several *Taenia* (21-23), *Echinococcus* (21, 22), *Fasciola* (24) and *Schistosoma* (25-30) species. However, the efficacy of these vaccines, measured as reduction of egg counts and/or worm burden (reviewed in (59)), was found to vary dramatically and is thus unpredictable.

Currently, no *Cooperia oncophora* vaccine exists. Several research groups have focused on the low-molecular weight proteins (12-16 kDa) as potential vaccine candidates, however without success (60-61; WO98/01550).

SUMMARY OF THE INVENTION

An object of the present invention is to provide vaccines for combating gastro-intestinal nematode infections in cattle and more specific *Cooperia* infections in cattle (bovine).

Another object of the present invention is to provide polynucleotides and proteins (or polypeptides) useful for preparing such vaccines.

One aspect of the invention relates to an isolated *Cooperia oncophora* protein or an immunogenic fragment of said protein, characterized in that said protein comprises or consists essentially of an amino acid sequence which has a sequence identity of at least 85%, preferably 90%, more preferably 95% to the amino acid sequence as depicted in SEQ ID NO: 1.

Also included in the present invention is an isolated nucleic acid sequence encoding said protein or immunogenic fragment, in particular a nucleic acid sequence having at least 85%, preferably 90%, more preferably 95% identity with the nucleic acid sequence as depicted in SEQ ID NO: 2.

A further embodiment relates to a recombinant DNA molecule comprising the herein described nucleic acid sequence, in particular further including a functionally linked promoter.

A further embodiment relates to a vector comprising the herein described nucleic acid sequence or recombinant DNA molecule, said vector in particular being a plasmid, bacteriophage, cosmid, virus or minichromosome.

The invention furthermore discloses a host cell comprising the herein described nucleic acid sequence, recombinant DNA molecule or vector, said host cell in particular being an animal cell, bacterial cell, yeast cell, insect cell or plant cell.

Another aspect the current invention relates to the protein or immunogenic fragment, the nucleic acid, the recombinant DNA molecule, the vector or the host cell, as described herein, for use as a medicine, more specific for use in the prevention or treatment of a *Cooperia oncophora* infection. Also the use of the protein or immunogenic fragment, the nucleic acid, the recombinant DNA molecule, the vector or the host cell, as described herein, for the manufacturing of a vaccine against *Cooperia oncophora* infection is part of the present invention.

A further embodiment relates to a vaccine against *Cooperia oncophora* infection, characterized in that said vaccine comprises or consists essentially of at least one protein or nucleic acid described herein (including combinations thereof), or a fragment of either, and a pharmaceutically acceptable carrier or diluents, said vaccine optionally comprising an adjuvant.

The invention furthermore relates to a method of vaccinating an animal against infection from a parasitic nematode, said method comprising the step of administering a purified or recombinant activation-associated secreted (ASP) protein(s) from the nematode *Cooperia oncophora* to said animal in order to raise an immune response in said animal.

BRIEF DESCRIPTION OF THE DRAWINGS

FIG. 1. A-C: Nucleotide sequences encoding and amino acid sequences of C. oncophora double-domain activation-associated secreted proteins; D: Nucleotide sequences encoding and amino acid sequences of *C. oncophora* double-domain activation-associated secreted proteins including C- and N-termini.

DETAILED DESCRIPTION OF THE INVENTION

Figure 2:
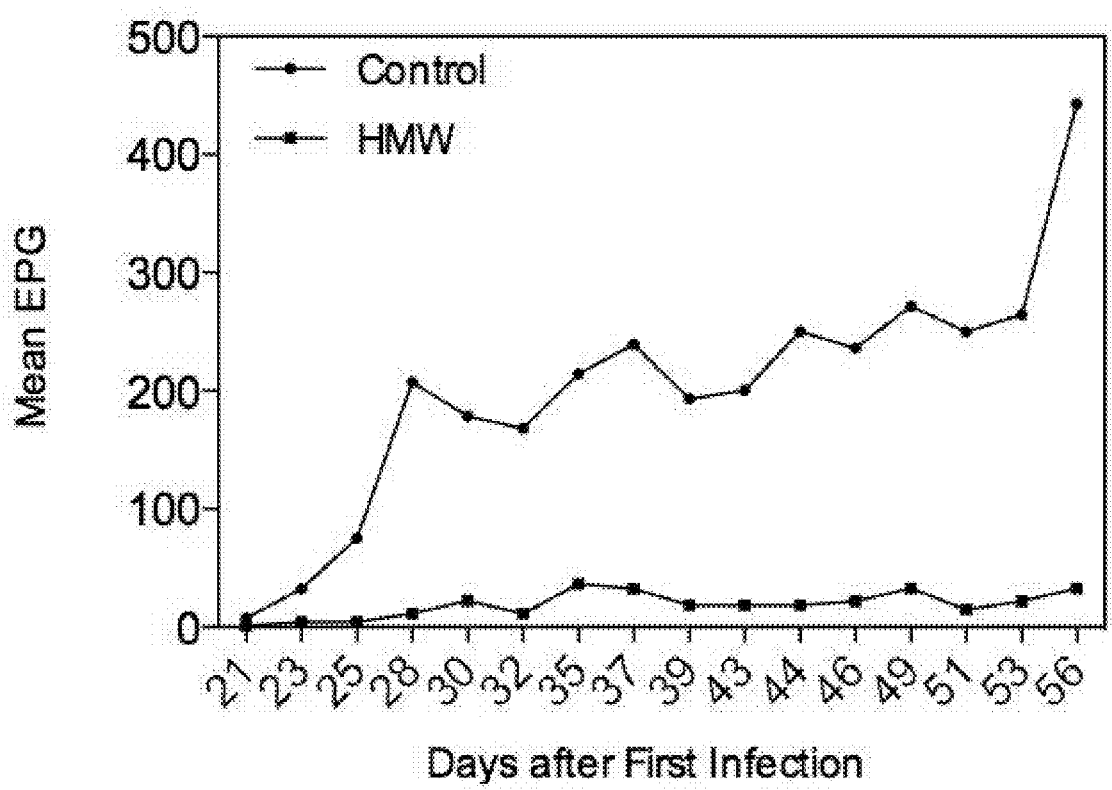
FIG. 2. Mean EPG output post-infection. *C. oncophora* eggs per gram faeces were recorded as a function of time, starting 21 days after the first infection, for the groups vaccinated with adjuvant (control) and the High Molecular Weight (HMW) excretone/secretone (ES) fraction.

The present invention envisions the development of prophylactic vaccines based on the proteomic identification, characterization and immunological evaluation of helminth antigens in the excretome/secretome (ES) that are the target of a protective immune response in the host. In essence, the ES fraction is secreted from the worm through oral openings and/or its outer surface and basically consists of a pool of proteins and other compounds crucial in helminth survival and propagation, host infection and evasion of host immunological responses (31, 32).

The invention provides isolated polynucleotides coding for excretory secretory (ES) proteins of adult stage *Cooperia oncophora* (*C. oncophora*) having an approximate molecular weight of 70 kD as estimated by SDS-PAGE, and identified as double-domain activation-associated secreted proteins (ASPs); including analogues, homologues, derivatives, parts or combinations thereof; which proteins are capable of conferring protective immunity on a host against infection by a parasitic nematode.

In one aspect, the current invention relates to an isolated nucleic acid sequence (also referred to as polynucleotide) comprising or consisting essentially of a nucleic acid sequence encoding a *C. oncophora* double-domain activation-associated secreted protein (ASP), or a part of said nucleic acid sequence that encodes an immunogenic fragment of said protein. In particular, the nucleic acid sequence or said part thereof is at least 85% identical to the nucleic acid sequence of the *C. oncophora* ASP gene as depicted in SEQ ID NO: 2. Even more particular, the nucleic acid sequence of the present invention further comprises at the N- and C-terminus, respectively, one or both of the sequences CTTTGCTCGCTTGATAATGGAATGACA (SEQ ID NO: 12) and GATGAAGATTGTAAGTGCAGCTCCTGCA-GATGCAGCACACAATTATCCATGTG TAT-CAACCCTAAC (SEQ ID NO: 13). Examples of said nucleic acids are represented by SEQ ID NO: 19, 20 and 21. In a particular embodiment, the nucleic acid sequence of the invention, or a part thereof, is at least 85% identical to the nucleic acid sequence of the *C. oncophora* ASP gene as depicted in SEQ ID NO: 19.

Preferably, the nucleic acid sequence according to the invention encoding the *C. oncophora* protein, or a part of that nucleic acid sequence that encodes an immunogenic fragment of that protein, is at least 90%, preferably 93%, more preferably 94%, 95%, 96%, 97%, 98%, 99% or even 100% identical to the nucleic acid sequence of the *C. oncophora* ASP gene as depicted in SEQ ID NO: 2 or SEQ ID NO:19. Nucleic acids having at least 98% identity with the nucleic acid sequence as depicted in SEQ ID NO: 2, are represented by SEQ ID NO: 4 and SEQ ID NO: 6. Nucleic acids having at least 98% identity with the nucleic acid sequence as depicted in SEQ ID NO: 19, are represented by SEQ ID NO: 20 and SEQ ID NO: 21.

In a further embodiment the current invention relates to an isolated *C. oncophora* protein and an immunogenic fragment thereof, wherein the amino acid sequence of the protein or immunogenic fragment is at least 90%, preferably 93%, more preferably 94%, 95%, 96%, 97%, 98%, 99% or even 100% identical to the amino acid sequence as depicted in SEQ ID NO: 1. Proteins having at least 98% identity with the amino acid sequence as depicted in SEQ ID NO: 1, are represented by SEQ ID NO: 3 and SEQ ID NO: 5. The invention also includes an isolated protein comprising or consisting essentially of the above identified amino acid sequence and a further N-terminus and/or C-terminus preferably characterized by the amino acids LCSLDNGMT (SEQ ID NO: 14) and DEDCKCSSCRCSTQLSMCINPN (SEQ ID NO: 15), respectively. Examples of said proteins are represented by SEQ ID NO: 16, 17 and 18. Hence in a specific embodiment the current invention relates to an isolated *C. oncophora* protein and an immunogenic fragment thereof, wherein the amino acid sequence of the protein or immunogenic fragment is at least 90%, preferably 93%, more preferably 94%, 95%, 96%, 97%, 98%, 99% or even 100% identical to the amino acid sequence as depicted in SEQ ID NO: 16, as well as to a nucleic acid encoding said protein, in particular as represented by SEQ ID NO: 19.

The percentage identity of nucleic acid and polypeptide sequences can be calculated using commercially available algorithms, which compare a reference sequence with a query sequence. The following programs (provided by the National Center for Biotechnology Information) may be used to determine homologies/identities: BLAST, gapped BLAST, BLASTN and PSI BLAST, which may be used with default parameters.

The term "isolated" is used to indicate that a cell, peptide or nucleic acid is separated from its native environment. Isolated peptides and nucleic acids may be substantially pure, i.e. essentially free of other substances with which they may bound in nature.

The term "fragment" as used herein refers to partial amino acid sequences (and nucleic acid sequences coding therefore) having at least one immunologic or immunogenic property in common with the native molecule. Such fragments will include at least one epitope (or antigenic determinant) of the native molecule. Normally, they will have a length of at least 8 amino acids, preferably at least 15 or 20 amino acids.

Since the present invention discloses nucleic acid sequences encoding novel *C. oncophora* proteins, it is now for the first time possible to obtain these proteins in sufficient quantities. This can e.g. be done by using expression systems to express the whole or parts of the genes encoding the proteins or immunogenic fragments thereof according to the invention.

Therefore, in a further embodiment, the invention relates to DNA fragments comprising a nucleic acid sequence according to the invention. A DNA fragment is a stretch of nucleotides that functions as a carrier for a nucleic acid sequence according to the invention. Such DNA fragments can e.g. be plasmids, into which a nucleic acid sequence according to the invention is cloned. Such DNA fragments are e.g. useful for enhancing the amount of DNA for use as a primer and for expression of a nucleic acid sequence according to the invention, as described below.

According to a further embodiment of the present invention the ASP protein is produced by the expression of a polynucleotide as described herein. Suitable vectors for expression of proteins are plasmids, bacteriophages, cosmids, viruses, minichromosomes or stably integrating vectors; the latter in particular for plant or animal cells. Generally these vectors have the property of autonomous replication except for the stably integrating vectors which insert themselves in the genetic material of the host cell and replicate with host's genetic material. Suitable host cells for the expression of proteins may either be prokaryotic or eukaryotic, such as but not limited to bacteria such as *Escherichia coli*, yeasts such as *Saccharomyces cerevisiae* and *Pichia pastoris*, mycoplasma's, algae, plant cells such as *Arabidopsis thaliana*, vertebrate cells, or baculovirus/insects cells; the plant or animals cells may be cultivated in vitro or may form part of an intact plant or animal, respectively. The recombinant polynucleotide may contain as an insert a complete polynucleotide coding for the ASP or a fragment thereof. Bacterial, yeast, fungal, insect, plant and vertebrate cell expression systems are very frequently used systems. Such systems are well known in the art and generally available. Vectors may also be used as a way of transporting the nucleic acid sequence into a target cell. In this regard, viruses often used as vectors are Vaccinia viruses (62), Herpesviruses (EP0473210), Adenoviruses and Retroviruses (69). A particular example in the context of the present invention is a bacterial vector. Herein bacteria capable of colonizing ruminants are transformed in order to enable them to express the ASP in such a way that it will lead to an immunogenic response against the parasite. In particular to elicit a strong local immune response at the mucosal surface of the gastrointestinal tract where these parasites usually reside. Suitable bacteria for this purpose are e.g. *Salmonella* and *Lactobacillus* bacteria.

An essential requirement for the expression of the nucleic acid sequence is an adequate promoter functionally linked to the nucleic acid sequence, so that the nucleic acid sequence is under the control of the promoter. It is obvious to those skilled in the art that the choice of a promoter extends to any eukaryotic, prokaryotic or viral promoter capable of directing gene transcription in cells used as host cells for protein expression. Therefore, a particular embodiment relates to a recombinant DNA molecule comprising a DNA fragment and/or a nucleic acid sequence according to the invention wherein the nucleic acid sequence according to the invention is placed under the control of a functionally linked promoter.

This can be obtained by means of e.g. standard molecular biology techniques, e.g. Sambrook & Russell: "Molecular cloning: a laboratory manual" (2001), Cold Spring Harbor Laboratory Press. Functionally linked promoters are promoters that are capable of controlling the transcription of the nucleic acid sequences to which they are linked. Such a promoter can be the native promoter of the ASP gene or another promoter of *Cooperia oncophora*, provided that that promoter is functional in the cells used for expression. It can also be a heterologous promoter. When the host cells are bacteria, useful expression control sequences, which may be used, include the Trp promoter and operator (63); the lac promoter and operator (64); the outer membrane protein promoter (65); the bacteriophage lambda promoters and operators (66); the [alpha]-amylase (*B. subtilis*) promoter and operator, termination sequences and other expression enhancement and control sequences compatible with the selected host cell. When the host cells are yeasts, useful expression control sequences, which may be used, include AOX promotor. When the host cells are plants, useful expression control sequences, which may be used, include phaseolin promotor (67).

Hence the present invention relates to a vector or host cell comprising a nucleic acid sequence encoding a protein according to the invention, and a recombinant DNA molecule comprising such a nucleic acid sequence under the control of a functionally linked promoter. This form also relates to a host cell containing a vector comprising a nucleic acid molecule encoding a *C. oncophora* protein or an immunogenic fragment thereof according to the invention.

The invention furthermore relates to a process for transforming a host to provide a transformed host, which process comprises providing a host, making the host competent for transformation, and introducing into the host a recombinant DNA molecule as described herein. The invention also encompasses the expression product of said transformed host. Preferably the expression product is in purified form.

In another aspect, the present invention provides a method of protecting a host from infection by a parasitic nematode which method comprises administering to the host at least one protein, nucleic acid or vector as described herein.

A particular embodiment provides a composition or a vaccine for raising an immune response in a subject. Vaccines may be used therapeutically, or prophylactically i.e. to prevent parasitic infection, in particular infection with species of the genus *Cooperia*, more in particular *Cooperia oncophora*. In specific cases the vaccine provided by this invention may be used in a method to prevent or reduce infection or colonisation of a host by a nematode parasite.

In particular, the nucleic acids, proteins or vectors as described herein are used to manufacture a composition or a vaccine, which typically include a pharmaceutically acceptable carrier, diluents and/or excipient, and optionally an adjuvant. It is accordingly an object of the present invention to provide a pharmaceutical composition or a vaccine against *C. oncophora* comprising, consisting essentially of, or consisting of:

a therapeutically effective amount of a nucleic acid sequence, protein, vector or host cell according to the invention;

a pharmaceutically acceptable carrier or diluent, and optionally an adjuvant.

The particular pharmaceutically acceptable carriers or diluents employed are "veterinary-acceptable" carriers or diluents and are conventional in the art. These include any and all solvents, dispersion media, coatings, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose. Stabilizers include e.g. albumin. Adjuvants are known to act in a number of different ways to enhance the immune response. In general, immunomodulatory adjuvants cause a general up-regulation of certain cytokines and a concomitant down regulation of others leading to a cellular Th1 and/or a humoral Th2 response.

As used in the present invention, "adjuvants" include, but are not limited to Quil A, ISCOM, ISCOMATRIX, the RIBI adjuvant system (Ribi Inc.), alum, aluminum hydroxide gel, Cholesterol, oil-in water emulsions, water-in-oil emulsions such as, e. g., Freund's complete and incomplete adjuvants, Block co-polymer (CytRx, Atlanta GA), SAF-M (Chiron, Emeryville Calif.), AMPHIGENO adjuvant, saponin, saponin in combination with a sterol (see e.g. US20050220814), QS-21 (Cambridge Biotech Inc., Cambridge Mass.), GPI-0100 (Galenica Pharmaceuticals, Inc., Birmingham, Ala.) or other saponin fractions, polymers such as diethyl-aminoethyl (DEAE)-dextran, polyethelyne glycol, and polyacrylic acid (e.g., CARBOPOL®),N-(2-Deoxy-2-L-leucylamino-b-D-glucopyranosyl)-N-octadecyldodecanoylamide hydroacetate (also known by the trade name Bay R1005®), monophosphoryl lipid A, Avridine lipidamine adjuvant, heat-labile enterotoxin from *E. coli* (recombinant or otherwise), cholera toxin, muramyl dipeptide, or immunomodulators such as cytokines and TLR agonists, cytosine-phosphate-guanosine (CpG) containing oligonucleotides, and combinations of these adjuvants. A preferred adjuvant is a saponin or the adjuvant may include a saponin, such as Quil A. In some embodiments, the adjuvant is a compound adjuvant which may comprise a saponin, and optionally a sterol, at least one of a polyacrylic polymer, a quaternary amine (e.g., DDA or avridine), a Th2 stimulant such as N-(2-Deoxy-2-L-leucylamino-b-D-glucopyranosyl)-N-octadecyldodecanoylamide, and/or an immunostimulatory oligonucleotide.

The adjuvanting compounds described above may be present in the form of an oil-in-water emulsion, wherein droplets of oil are dispersed in a continuous aqueous phase. In other aspects, the adjuvant may be oil-based, i.e., it may contain a continuous oily phase and droplets of aqueous phase interspersed therein. Emulsion adjuvants can preferably be microfluidized to achieve a smaller (submicron) size and a greater uniformity among the emulsion particles, thus resulting in emulsion stability and may even increase the adjuvanting effect of such microfluidized emulsion.

U.S. Pat. No. 5,961,970 teaches yet another submicron oil-in-water emulsion to be used as a vaccine adjuvant. In said emulsion, the hydrophobic component is selected from the group consisting of a medium chain triglyceride oil, a vegetable oil and a mixture thereof. The surfactant included in this emulsion can be a natural biologically compatible surfactant such as phospholipid (e.g., lecithin) or a pharmaceutically acceptable non-natural surfactant such as TWEEN-80.

U.S. Pat. No. 5,084,269 teaches that an adjuvant formulation containing lecithin in combination with mineral oil causes a decrease in irritation within the host animal and simultaneously induces increased systemic immunity. The adjuvant formulation resulting from U.S. Pat. No. 5,084,269 is commercially used in veterinary vaccines under the trade name AMPHIGEN®. The AMPHIGEN® formulation is made up of micelles-oil droplets surrounded by lecithin.

Thus, in different embodiments, the instant invention provides a composition comprising an antigen component, and an adjuvant component. The antigen component may comprise a HMW ES subfraction, an amino acid sequence at least 90% (e.g., at least 93% or at least 94% or at least 95% or at least 96%, or at least 97%, or at least 98%, or at least 99% or 100%) identical to SEQ ID NO: 1 or SEQ ID NO: 16, or a nucleic acid sequence at least 90% (e.g., at least 93% or at least 94% or at least 95% or at least 96%, or at least 97%, or at least 98%, or at least 99% or 100%) identical to SEQ ID NO: 2 or SEQ ID NO:19, or any combination thereof. The adjuvant component may contain a saponin (such as, for example, Quil A), and optionally a sterol (such as, for example, lanosterol, ergosterol, or cholesterol), at least one of a quaternary amine (such as, for example, DDA or avridine), a polyacrylic polymer, the glycolipid (e.g., BayR1005®), and/or an immunostimulatory oligonucleotide. Additionally or alternatively the adjuvant component may contain an oil-in-water emulsion. In yet other embodiments, the water-in-oil emulsion may contain an immunostimulatory oligonucleotide and DEAE dextran. The amounts and concentrations of adjuvants and additives useful in the context of the present invention can readily be determined by the skilled artisan.

Preferably, the composition as described herein is an immunogenic composition. By "immunogenic" is meant the capacity to provoke an immune response in a subject against the pathogen. The present invention accordingly provides compositions for use in eliciting an immune response which may be utilized as a vaccine against *C. oncophora*. The immune response can be a cellular immune response mediated primarily by NK cells, cytotoxic T-cells, or a humoral immune response mediated primarily by helper T-cells, which in turn activates B-cells leading to antibody production. More specific, by "eliciting or inducing an immune response" is meant that an antigen stimulates synthesis of specific IgG1 antibodies and/or cellular proliferation as measured by, for example, $^3$H thymidine incorporation of NK cells, T-cells and B-cells. Administering the vaccine of the invention elicits an immune response that results in a reduction in mean cumulative fecal egg count of at least about 60% in an animal in relation to a non-vaccinated (e.g. adjuvant alone) control animal. Preferably, the level of the decrease is about 70%, more preferably about 80% and most preferably, about 90% or greater. Hence the immune response confers some beneficial, protective effect to the subject against a subsequent challenge with the infectious agent. More preferably, the immune response prevents the onset of or ameliorates at least one symptom of a disease associated with the infectious agent, or reduces the severity of at least one symptom of a disease associated with the infectious agent upon subsequent challenge. Symptoms associated with *C. oncophora* infections typically include, but are not limited to diarrhea and ill thrift.

By "subject" or "host" is meant any animal that is susceptible to *C. oncophora*, such as cattle. The term "cattle" refers to bovine animals including but not limited to steer, bulls, cows, and calves.

In practicing the present methods, a vaccine or composition of the present invention is administered preferably via intramuscular or subcutaneous routes, although other routes of administration can be used as well, such as e.g. by oral, intranasal (e.g. aerosol or other needleless administration), intra-lymph node, intradermal, intraperitoneal, rectal or vaginal administration, or by a combination of routes. The formulation of the composition or the vaccine can be made in various forms depending upon the route of administration.

For example, the compositions can be made in the form of sterile aqueous solutions or dispersions suitable for injectable use, or made in lyophilized forms using freeze-drying techniques. Lyophilized immunogenic compositions are typically maintained at about 4° C., and can be reconstituted in a stabilizing solution, e.g. saline or and HEPES, with or without adjuvant.

Boosting regimens may be required and the dosage regimen can be adjusted to provide optimal immunization. Immunization protocols can be optimized using procedures well known in the art. A single dose can be administered to animals, or, alternatively, two, three or more inoculations can take place with intervals of two to ten weeks. Depending on the age of the animal, the immunogenic or vaccine composition can be re-administered. For example, the present invention contemplates the vaccination of healthy calves (3-12 months of age) 6 and/or 3 weeks prior to their first grazing season and revaccination at the beginning of the first grazing season.

The term "therapeutically effective amount" refers to an amount sufficient to elicit an immune response in the animal to which it is administered. The immune response may comprise, without limitation, induction of cellular and/or humoral immunity. The amount of a vaccine that is therapeutically effective may vary depending on the condition of the cattle and/or the degree of infection, and can be determined by a veterinary physician. The extent and nature of the immune responses induced in the cattle can be assessed by using a variety of techniques. For example, sera can be collected from the inoculated animals and tested for the presence of antibodies specific for C. oncophora.

In addition to the above described aspects of the invention and including the given descriptions of all modifications and means of production and administration, a composition or vaccine can be provided on the C. oncophora ASP proteins or polynucleotides as described herein as single polypeptides or polynucleotides, or used in combination.

As such, in some embodiments, the method, use, composition or vaccine of the present invention can be based on two or more ASP proteins as described herein, or fragments thereof. In a specific embodiment, at least two, three or more ASP proteins, or nucleic acids encoding said proteins, or fragments thereof, are used in a single composition or vaccine. As such, in some embodiments, the present invention relates to a composition or vaccine based on, comprising, consisting essentially of, or consisting of at least two ASP proteins having at least 85% identity with the amino acid sequence as represented by SEQ ID NO: 1 or SEQ ID NO: 16; or at least two ASP nucleic acids having at least 85% identity with the nucleotide sequence as represented by SEQ ID NO: 2 or SEQ ID NO: 19; or fragments thereof. In a specific embodiment, the composition or vaccine comprises two or three of the proteins selected from the group consisting of the amino acid sequence as represented by SEQ ID NO: 1, 3, 5, 16, 17 and 18 and; or two or three of the nucleic acids encoding these proteins, or as represented by respectively SEQ ID NO: 2, 4, 6, 19, 20 and 21. Examples of specific protein combinations are: SEQ ID NO: 1 and 3; SEQ ID NO: 1 and 5; SEQ ID NO: 3 and 5; and SEQ ID NO: 1, SEQ ID NO: 3 and SEQ ID NO: 5; or the nucleic acids encoding these proteins and as provided herein.

This invention will be better understood by reference to the Experimental Details that follow, but those skilled in the art will readily appreciate that these are only illustrative of the invention as described more fully in the claims that follow thereafter. Particular embodiments and examples are not in any way intended to limit the scope of the invention as claimed. Additionally, throughout this application, various publications are cited. The disclosure of these publications is hereby incorporated by reference into this application to describe more fully the state of the art to which this invention pertains.

EXAMPLES

1. Experimental Procedures 1.1 Preparation of Adult *Cooperia oncophora* Excretory and Secretory Products Calves were infected with 100,000 infectious larvae of an in-house *Cooperia* oncophora strain. Adult stage *Cooperia oncophora* were collected from the small intestine 21 days p.i. The worms were subsequently placed on a modified Baermann apparatus which was filled with 37° C. physiological water. Worms migrating to the bottom of the funnel were then collected and washed for a minimum of five times in physiological water at 37° C. In a next step, the helminths were transferred and cultured for three consecutive days in RPMI medium (Gibco®, Invitrogen; Carlsbad, Calif., USA) at 37° C. The medium was refreshed on a daily basis and stored at −80° C. After this three-day culturing period, all −80° C. stored media, containing the ES protein fraction, were passed through a 0.22 μm filter and simultaneously concentrated and dialyzed to PBS at 4° C. using an Amicon ultrafiltration unit and Ultracel Regenerated Cellulose ultrafiltration discs (both Millipore; Billerica, Mass., USA). The protein concentration of the obtained ES sample was determined using the BCA™ Protein Assay Kit (Pierce, Rockford, Ill., USA) according to the manufacturer's instructions.

1.2. Size Exclusion Chromatography

Size exclusion chromatographic (SEC) fractionation of *Cooperia oncophora* total ES material was carried out using a self-packed Superdex 200 16/70 column (GE Healthcare Bio-Sciences AB; Uppsala, Sweden). Maximum volumes of 0.5 mL of a concentrated ES protein solution (corresponding to 300 μg of ES protein) were injected and eluted in PBS at a flow rate of 1 mL/min. Protein elution was monitored by absorbance measurements at 280, 254 and 214 nm, and when suitable 1.0 mL fractions were collected (ÄKTA Explorer, GE Healthcare Bio-Sciences AB; Uppsala, Sweden). PBS column equilibration and washing steps of at least two column volumes were carried out prior to and after each experiment, respectively. To obtain adequate amount of proteins, multiple rounds of this procedure were performed.

1.3. One- and Two-Dimensional Electrophoresis and Tryptic Digestion of ES Proteins Denaturing one-dimensional electrophoresis (SDS-PAGE) was carried out according to Laemmli (34), including and omitting β-mercaptoethanol in reducing and non-reducing SDS-PAGE, respectively. Native one-dimensional gel electrophoresis was performed with the samples dissolved in 60 mM Tris pH 6.8, 0.1% bromophenol blue and 20% glycerol sample buffer with electrophoresis running conditions as follows: separating and stacking gels consisted of Tris-HCl pH 8.5 and Tris-$H_3PO_4$ pH 9.6, respectively, with proper amounts of acrylamide-bisacrylamide added, whereas the running buffer was a Tris-Glycine buffer at pH 8.9 and the voltage was set at 90 V.

Two-dimensional gel electrophoresis was carried out as follows. Protein was precipitated by adding five volumes of ice-cold acetone to one volume of ES protein. This was vortexed briefly and incubated at -20° C. for one hour, after which the protein pellet was recovered by centrifugation at 5,000 rpm for five minutes. The supernatant was discarded and the pellet allowed to air-dry, after which it was resolubilized in 8 M urea, 2 M thiourea, 2% w/v CHAPS, 20 mM DTT, 0.2% v/v carrier ampholytes (pH 3-10; GE Healthcare Bio-Sciences AB; Uppsala, Sweden). This was left at room temperature for one hour, followed by centrifugation at 8,000 rpm for five minutes to remove any insoluble protein still present. The remaining supernatant, corresponding to approximately 150 µg of ES protein, was applied to 7 cm, pH 3-10, Immobiline™ DryStrip IEF strips (GE Healthcare Bio-Sciences AB; Uppsala, Sweden). Covered with mineral oil, this was left overnight at room temperature for rehydration of the strip and uptake of the protein sample. Isoelectric focussing was carried out at room temperature using an Ettan IPGphor3 isoelectric focussing instrument (GE Healthcare Bio-Sciences AB; Uppsala, Sweden) with an initial three hour focussing period at 300 V, followed by a five hour linear gradient from 300 to 3500 V and a final 18 h long time-span at 3500 V, yielding a total voltage load of approximately 73 kVh. Proteins resolved in the first dimension strips were reduced and alkylated prior to second-dimensional electrophoresis by incubating the strips for 15 minutes at room temperature in a 50 mM Tris-HCl, pH 8.8, 6 M urea, 30% v/v glycerol, 2% w/v SDS, 2% w/v DTT solution followed by another 15 minutes in an identical solution containing 2.5% w/v iodoacetamide instead of the DTT. The second-dimensional electrophoresis (SDS-PAGE), with the IEF strip embedded in the stacking gel, was carried out as described for 'one-dimensional gel electrophoresis'.

SimplyBlue™ SafeStain (Invitrogen; Carlsbad, Calif., USA) was used to visualize the proteins according to the manufacturer's instructions. Pore size of the gels, provided as a percentage of total acrylamide-bisacrylamide monomer concentration, is 13,5%.

Prior to tryptic digestion, protein bands and/or spots of interest were excised from the gel, washed twice for 20 minutes at 30° C. using a mixture of 50% acetonitrile (ACN)—200 mM ammonium bicarbonate, and then air-dried. Sequencing grade trypsin (Promega; Madison, Wis., USA) was added to a final amount of 0.1 µg and the trypsin-gel slice mixture was then kept on ice for 45 minutes, after which 50 mM ammonium bicarbonate was added until the gel slices were completely submerged. Digestion was performed by overnight incubation at 37° C. Peptides were extracted by adding 60% ACN-0.1% formic acid twice to the gel spots. The extraction buffer was evaporated in a Speedvac apparatus with the remaining peptides being redissolved in 8 µL of 0.1% formic acid.

1.4. Mass Spectrometric Analysis

Tryptic peptides were spotted on a stainless steel matrix-assisted laser desorption ionization (MALDI) target plate and covered with α-cyano-4-hydroxycinnamic acid matrix (7 mg/mL in 50% ACN, 0.1% trifluoroacetic acid, 1 mM ammonium citrate) in a 1:1 ratio. Prior to each set of analyses, instrument calibration was carried out using Cal Mix (Applied Biosystems; Foster City, Calif., USA) according to the manufacturer's instructions. Protein identification was obtained by measuring the PMF on a MALDI-tandem time-of-flight mass spectrometry (MALDI-TOF/TOF MS) system (model 4800 proteomic analyser; Applied Biosystems; Foster City, Calif., USA) in positive ion MS mode. MS/MS was performed to verify the sequences of certain peptides.

1.5. Protein Identification

For peptide mass fingerprint analysis, the obtained spectra were searched against the *Cooperia oncophora* EST-based transcriptome database (33) consisting of 31,774 amino acid sequences, supplemented with existing NCBI depositions for *C. oncophora*, using the GPS Explorer™ V2 software platform (Applied Biosystems; Foster City, Calif., USA) which makes use of the Mascot search engine (Matrix Science Inc.; Boston, Mass., USA). The spectra were searched using a 200-ppm peptide mass and a 0.8-Da MS/MS tolerance, with carbamidomethylation (Cys) and methionine-oxidation as variable modification parameters and with a maximum tolerance of two missed cleavage events during trypsin digestion of the protein.

1.6. Sequence Analysis

Following their MS identification, non-full-length amino acid sequences were subjected to NemaBLAST search algorithms (33), yielding several neighboring and/or overlapping amino acid sequences. These were subsequently aligned using the MegAlign software (DNASTAR, Inc.; Madison, Wis., USA), employing the ClustalW alignment algorithm, in most cases leading to a significant increase in sequence coverage and mostly providing full-length amino acid sequences of the identified proteins. These sequences were then subjected to BLASTP analysis (35) employing a non-redundant protein sequence database to assign an identification based on sequence identity.

The double-domain ASP full-length sequence was determined as follows: two degenerate primers (forward, ATG-YAACAGKAYTGGGTGAGG (SEQ ID NO: 7) and reverse, ATACACATGGAYAAYTGTGTGCT (SEQ ID NO: 8), with Y and K representing T/C and G/T, respectively) were designed based on conserved regions in the putative double-domain ASP sequence. Polymerase chain reaction (PCR) using the GoTaq® enzyme (Promega; Madison, Wis., USA) was carried out by mixing 1 µL of adult-stage *Cooperia oncophora* cDNA with 1 µM of both forward and reverse primers and one unit of GoTaq® in reaction buffer containing 0.2 mM of each dNTP and 1.2 mM $MgCl_2$. PCR experiments were carried out on a Mastercycler® Ep instrument (Eppendorf; Hauppauge, N.Y., USA) where two minutes at a denaturing temperature of 95° C. were followed by 35 cycles of denaturing (30 seconds at 95° C.), annealing (30 seconds at 58° C.) and elongation (DNA synthesis for 90 seconds at 72° C.). Afterwards, a final elongation step at 72° C. for five minutes was included, after which the PCR mixtures were kept at 10° C. The obtained PCR products were subsequently ligated in pGEM®-T Easy (Promega; Madison, Wis., USA) according to the manufacturer's instructions, after which DH5α competent cells (Invitrogen; Carlsbad, Calif., USA) were transformed with these vector constructs as described by the manufacturer and plated on X-gal (5-bromo-4-chloro-indolyl-β-D-galactopyranoside) containing medium. Fifty-three white colonies were picked and analysed by mixing 15 µL of clone suspension (in water) with identical amounts of the reagents mentioned above. PCR conditions were also duplicated from the abovementioned, be it that only 32 cycles of denaturing, annealing and elongation were carried out. The obtained PCR fragments were sequenced (at the Genetic Service Unit, Ghent University Hospital), followed by matching of the obtained data to the previously recorded MS and MS/MS spectra.

1.7. In Silico Protein Characterization

Following full-length amino acid sequence assessment of the identified proteins, molecular weight and iso-electric point values were determined using the corresponding ExPASy calculation tools (SIB Bioinformatics Resource Portal), whereas N-terminal signal sequences were predicted using SignalP 3.0 (The Center for Biological Sequence Analysis at the Technical University of Denmark) (36) or, when lacking, non-classical secretory proteins were assessed using SecretomeP 2.0 (37). Regarding SignalP 3.0 predictions, identifications were considered positive when both neural network and hidden Markov model algorithms offered corroborative estimations. Non-classical secreted proteins were predicted to yield a neural network score exceeding the normal threshold of 0.5 but not to contain a signal peptide.

1.8. Release, Purification and Derivatization of N- and O-glycan Moieties

Total ES material as well as separate size exclusion chromatography-obtained ES fractions, i.e. HMW, MMW and LMW fractions, were subjected to serial treatment with PNGase F and PNGase A to obtain released N-glycans. To this end, lyophilized proteins were redissolved in PBS with 1.3% SDS and 0.1% β-mercaptoethanol, and incubated at 95° C. for 10 minutes, followed by addition of 1.3% NP-40. The samples were then incubated with trypsin-coupled Sepharose for 16 hours at 37° C. while shaking. Beads were spun down, the supernatant transferred to a fresh tube and PNGase F added, followed by incubation for 24 hours at 37° C. while shaking. The mixture was then applied to a $C_{18}$ RP cartridge (500 mg; JT Baker, Philipsburg, N.J., USA), and the flow-through and wash fractions (2 mL 10% acetonitrile (ACN) and 4 ml water, respectively) were subsequently applied to carbon cartridges (150 mg Carbograph; Grace, Deerfield, Ill., USA). After a wash with 6 mL of water, glycans were eluted with 3 mL of 25% ACN and 3 mL of 50% ACN containing 0.1% TFA. The (glyco)-peptides that remained on the $C_{18}$ RP cartridge were eluted by applying 5 mL of 30% ACN/0.1% TFA and 5 mL of 60% ACN/0.1% TFA, and these combined eluates were subsequently vacuum dried. The (glyco)-peptides were dissolved in sodium acetate (NaAc) pH 4.5 and, after addition of PNGase A (Roche Diagnostics GmbH, Mannheim, Germany), incubation for 24 hours at 37° C. The mixture was applied to a $C_{18}$ RP cartridge and a carbon cartridge as outlined above. The purified PNGase F- and PNGase A-released N-glycans in the carbon cartridge eluates were each subjected to labelling with 2-aminobenzoic acid (2-AA) as described previously (38). For clean-up, labelled glycan moieties were loaded on Biogel P-10 (BioRad, Veenendaal, The Netherlands) in 75% ACN and after washing with 80% ACN eluted with water. In parallel, to obtain O-glycan alditols, ES samples were treated with 0.1 M NaOH/1 M $NaBH_4$ at 40° C. for 24 hr. Samples were then neutralized on ice using 4 M acetic acid and boric acid was removed by repeated evaporation and addition of 1% acetic acid in MeOH. Released O-glycans were purified using $C_{18}$ and carbon cartridges as described above. For permethylation, dried O-glycans were dissolved in DMSO, after which NaOH (spatula-tip with powder) was added, and the sample was left at room temperature for 10 minutes while shaking regularly. Then, 100 µL of iodomethane was added, followed by 10 minutes of regular shaking and subsequently the addition of 400 µL of dichloromethane and 500 µL of water. Shaking by inversion, removal of the aqueous layer and addition of fresh water were repeated five times before the remaining organic layer was dried under a flow of nitrogen.

1.9. Excretome/Secretome Glycan Analysis by Mass Spectrometry

Employing the assembled amino acid sequences of the identified proteins, in silico N-linked glycan analyses performed using NetNGlyc 1.0 Server (Technical University of Denmark). Experimental glycan analyses were carried out as follows: 2-AA-labeled N-glycan and permethylated O-glycan pools were analyzed with an Ultraflex II MALDI-TOF mass spectrometer (Bruker Daltonics, Bremen, Germany) operating in the negative-ion (N-glycans) or positive-ion (O-glycan) reflectron mode using DHB (Bruker Daltonics) as a matrix. A sample of MMW N-glycans was incubated with Jack bean α☐mannosidase (Sigma) in NaAc pH 4.5 for 16 h at 37° C. and analysed by MALDI-TOF MS after application to Zip-Tip $C_{18}$ and direct elution onto the target plate with a solution of 20 mg/mL DHB in 30% ACN. For glycopeptide analysis, a sample of the tryptic glycopeptide/peptide mixture extracted from the gel slice was applied to a reverse-phase column (PepMap, 3 µm, 75 µm·100 mm; Dionex /LC Packings, Amsterdam, the Netherlands) using an Ultimate 3000 nano-LC system (Dionex /LC Packings). The column was equilibrated at room temperature with eluent A (0.1% formic acid in water) at a flow rate of 200 nL/min. After injection of the sample, elution conditions were switched to 10% solvent B (95% acetonitrile, 0.1% formic acid) followed by a gradient to 60% B in 45 min and a subsequent isocratic elution with a duration of 10 minutes. The LC column was coupled to an Esquire HCT-Ultra ESI-ion trap-MS (Bruker-Daltonics, Bremen, Germany) equipped with an online nanospray source operating in the positive-ion mode. For electrospray (1100-1250 V), electropolished stainless steel LC/MS emitters (150 µm OD, 30 µm ID) from Proxeon A/S (Odense, Denmark) were used. The solvent was evaporated at 175° C. employing a nitrogen stream of 7 L/min. Ions from m/z 500 to m/z 1800 were registered in the MS mode. When operated in the auto MS/MS mode, registering ions from m/z 140 to 2200, each MS scan was followed by the acquisition of MS/MS spectra of up to three of the most abundant ions in the MS spectrum.

1.10 Vaccination Trial

Fourteen male MontBéliard calves, aged 7 months of age at the start of the experiment, were randomized over two groups of seven animals. Housing of the animals, feeding, immunizations with the HMW fraction, challenge infections, faecal egg counts and worm length assessments were carried out as described previously (39), except that in this study animals were immunized with 30 µg protein and 750 µg adjuvant at each immunization. Animals were bled before the start of the trial, and one week after the second and third immunizations. All parasitological techniques were performed blindly, that is without knowledge of the treatment group that the animal belonged to.

1.11 Antibody Responses

An enzyme-linked immunosorbent assay (ELISA) was employed to determine serum immunoglobulin IgG1 and IgG2 levels against *C. oncophora*. The HMW adult ES fractions was separately coated (1 µg/mL) on an ELISA 96-well plate overnight in carbonate buffer (0.025 M, pH 9.6), then blocked overnight in a phosphate buffered saline (PBS) solution with 0.2% Tween80 and 2% bovine serum albumin (BSA) added, followed by incubation with serum from either the control group (adjuvant only) or the corresponding immunized group (antigen with adjuvant) (serial dilution series of 1/200 in PBS with 0.2% Tween80 and 2% BSA). Sheep anti-bovine IgG1 and IgG2 coupled to horseradish peroxidase (HRP; Sigma-Aldrich; St. Louis, Mo., USA) were used as conjugates (all diluted 1:200 in PBS with 0.2% Tween80 and 2% BSA), with ABTS as the substrate. Optical density was measured at 405 nm with the 492 nm signal serving as a blank.

1.12. Statistical Analyses

Data are presented as arithmetic means. The significance of differences between vaccinated groups and the adjuvant control group was pairwise assessed using a one-tailed Mann-Whitney U-test. Differences between groups were considered statistically significant provided that the corresponding P-value was smaller than 0.05.

1.13 Expression in *Pichia pastoris*

The protein coding sequence are PCR amplified from *C. oncophora* cDNA and subsequently inserted as a XhoI-NotI fragment in the Pichia expression vector pPIC9 (Invitrogen Ltd, Paisley, UK). The resulting expression plasmid, pPIC9-OoASP1, are used to transform a *Pichia pastoris* GnM5 strain (68) by electroporation. Individual clones growing on minimal plates are isolated and tested for secretion of the recombinant proteins by SDS-PAGE followed by Coomassie Brilliant Blue staining and immunoblotting. The glycoform of the secreted proteins is assessed using DSA-FACE glycan profiling (68). Individual clones are subsequently selected on YPD plates containing nourseothricin and tested for recombinant protein secretion and used to inoculate a shake flask culture with BMGY medium. After 48 hours of growth at 28° C., the cells are pelleted by centrifugation for 5 minutes at 1,519 ×g after which the cells are resuspended in BMMY and further grown at 28° C. Every 12 hours extra methanol (0,5%) is added to the culture and after 48 hours of induction the cells are finally pelleted. The cell medium is harvested and filtered over a 0.2 μm membrane. Upon addition of ammonium sulphate to 50% saturation at 4° C., the recombinants are precipitated and concentrated in a pellet fraction by centrifugation at 18,000 ×g for 15 minutes. This pellet is dissolved in 40 mM sodium acetate buffer (pH 4.4) and the remaining ammonium sulphate removed by gel filtration using a Sephadex G25-column (GE Healthcare Bio-Sciences AB; Uppsala, Sweden). This fraction is then applied to a SP-Sepharose-column (GE Healthcare Bio-Sciences AB; Uppsala, Sweden) equilibrated in 40 mM sodium acetate buffer (pH 4.4) and the bound recombinants eluted employing a gradient to 1 M sodium chloride (NaCl) in the same buffer. Fractions containing recombinant protein are pooled, dialysed to 25 mM Tris-HCl (pH 7.5) and loaded on a MonoQ-column (GE Healthcare Bio-Sciences AB; Uppsala, Sweden). The recombinants are eluted from this column using a gradient to 1 M NaCl in the same buffer. Fractions containing recombinant ASPs are pooled and buffer-exchanged to PBS by gel filtration on a Sephadex G25-column (GE Healthcare Bio-Sciences AB; Uppsala, Sweden).

1.14. Field Trial

The trial consists of two groups of 12 Holstein-Friesian calves each. Twenty four helminth-naive calves, 7 to 9 months old, were randomly divided in twelve pairs. Each pair was randomly assigned to a treatment group (control or vaccinated). Immunizations with the HMW fraction and faecal egg counts were carried out as described in the vaccination trial. One group was vaccinated three times with three weeks interval with the *C. oncophora* HMW/Asp vaccine in combination with QuilA whereas the other one was injected three times with QuilA only. After the last vaccination, all animals were put on a pasture that was naturally contaminated with infective larvae of *Cooperia oncophora* and that was divided in 12 identical plots. Two animals belonging to the same group (Control or vaccinated) were randomly assigned to a plot, so 6 plots for the control animals and 6 plots for the vaccinated animals. Faecal samples from the animals were collected weekly to determine *C. oncophora* egg production.

2. Results 2.1. The Adult-Stage *Cooperia oncophora* Excretome/Secretome

For reasons of obtaining adequate in-gel resolution and thorough protein separation on the one hand, without compromising in sensitivity, more specifically detecting low-abundance proteins, on the other hand, we sought to apply two complementary techniques. In first instance, two-dimensional gel electrophoretic (2D-GE) separation of the adult-stage *Cooperia oncophora* ES protein fraction revealed twenty-five clearly visible protein spots, grouped in three clusters termed HMW, MMW and LMW representing the high, medium and low molecular weight protein pools to which they respectively belong. All spots were excised and subjected to matrix-assisted laser desorption ionization mass spectrometry (MALDI-MS)-directed identification, resulting in the successful annotation of twenty-two spots (88% success ratio). As summarized in Table 1 (and Table S1), more than 90% of the HMW fraction consists of a double-domain activation-associated secreted protein-like protein (ASP), displaying some heterogeneity in terms of iso-electric point (pI) values. As for protein content, the MMW and LMW protein clusters appear to contain a broader range of proteins. More particularly, the MMW fraction was found to contain three distinct proteins, i.e. innexin, thioredoxin peroxidase and an activation-associated secreted protein (ASP), here in a single-domain conformation [40]. The LMW protein pool, on the other hand, despite displaying a multitude of protein spots, in fact covers two proteins with as of yet unknown functions and three previously documented low-molecular weight ES antigens/proteins, known as 14-kDa ES antigen, ES antigen 1 and ES antigen 2 (Table 1). Given the high degree of complexity in terms of 2D-GE spot number and distribution, the latter are expected to bear extensive amino acid sequence variation and/or chemical modifications, thereby yielding a considerable number of protein isoforms both in terms of molecular mass and pI values.

In parallel to 2D electrophoretic analysis we chose to fractionate the adult *C. oncophora* ES proteome by size exclusion chromatography (SEC) mainly for two reasons: i) by applying such a preparative workflow, sufficient amounts of all three fractions (HMW, MMW and LMW) were obtained, and ii) through one-dimensional gel electrophoretic (1D-GE) analysis of the SEC-obtained fractions low-abundance proteins, which may have been undetectable or masked in 2D-GE, should become more visible and may thus expand the obtained dataset. Indeed, whereas overall a similar protein distribution was noted upon comparison of the two methodologies, SEC fractionation followed by 1D-GE analysis did reveal the presence of a number of additional ES proteins. As summarized in Table 1 (and Table S2), mass spectrometric identification of the protein-bands demonstrated that, besides the double domain ASP, the HMW portion additionally holds very low amounts of a 'hypothetical protein', which curiously was observed only under reducing conditions. Similarly, our size exclusion chromatographic approach unmasked two additional proteins in the MMW protein pool, particularly aldose reductase and the parasitic stage specific protein 2, the latter with no further functional information currently available. In contrast to the HMW and MMW fractions, the low molecular weight pool was not revealed to contain any additional proteins to those revealed upon 2D-PAGE analysis.

Notably, both the double- and the single-domain ASPs were observed to migrate as doublets upon one-dimensional gel electrophoretic separation of the HMW and MMW fractions, respectively (data not shown).

TABLE 1

MS-directed annotation of the adult-stage *Cooperia oncophora* excretome/secretome. The top, middle and lower parts of the table reflect the HMW, MMW and LMW ES fractions, respectively.

| Homology-based ID[a] | Spots | Bands | Secr. pred . . . [b]/ N-glyc. (#)[c] | $M_r$/pI[d] (kDa/—) |
|---|---|---|---|---|
| Double-domain ASP | 1-4 | 1-3 | SP/Y (2) | 53.2/7.67 |
| Hypothetical protein | | 4 | — | — |
| Aldose reductase | | 5 | N/Y (2) | 35.5/8.32 |
| Single-domain ASP | 5 | 6, 7 | SP/Y (1) | 30.3/6.26 |
| Innexin | 6 | | — | — |

TABLE 1-continued

MS-directed annotation of the adult-stage *Cooperia oncophora* excretome/secretome. The top, middle and lower parts of the table reflect the HMW, MMW and LMW ES fractions, respectively.

| Homology-based ID[a] | Spots | Bands | Secr. pred . . . [b]/ N-glyc. (#)[c] | $M_r$/pI[d] (kDa/—) |
|---|---|---|---|---|
| Thioredoxin peroxidase | 7 | | N/N | 21.8/6.90 |
| Parasitic stage specific protein 2 | | 8 | NC/N | 16.4/7.14 |
| 14 kDa ES protein | 10, 24 | 11 | NC/Y (1) | 14.5/8.54 |
| ES antigen 2 protein | 11, 12, 19 | | NC/N | 13.2/5.49 |
| ES antigen 1 | 13-16, 18, 20, 21 | 10, 12 | SP/N | 13.9/5.30 |
| Unknown 1 (isotig32303) | 8 | 9 | SP/N | 12.3/4.69 |
| Unknown 2 (isotig10739) | 9, 23 | | SP/N | 14.7/8.22 |

[a]Based on BLASTP-search

[b]Prediction of protein secretion using the full-length protein sequences as determined in this study or when available at GenBank (indicated with an asterisk). SP: presence of a signal peptide as determined by SignalP 3.0; NC: non-classical secretory protein as determined by SecretomeP 2.0; N: not secreted

[c]The presence of possible N-glycosylation sites as determined by NetNGlyc 1.0 analysis using the full-length protein sequences as determined in this study (Y: yes; N: no) (number of consensus sites found in the amino acid sequence is given between brackets)

[d]$M_r$ and pI values were determined using the ExPASy molecular weight and iso-electric point calculation tool. Values corresponding to full-length proteins are provided. Cleavage of possible signal peptide was not taken into account.

TABLE S1

MS-directed annotation of the *Cooperia oncophora* ES proteome, as revealed by 2D-PAGE.

| Spot N° | In-house database ID | GenBank Acc. N° | Organism (closest homology) | E-value BLASTP | MALDI-MS Mowse score | MS sequence coverage (%) | Matched peptides | Un-matched peptides | MS² sequence coverage (%) | Description (top BLASTP hit) |
|---|---|---|---|---|---|---|---|---|---|---|
| 1 | contig05709 | AAK35199.1 | *C. punctata* | 3E−94 | 106 | 20 | 6 | 15 | 5 | ASP-like protein |
| 2 | contig05709 | AAK35199.1 | *C. punctata* | 3E−94 | 198 | 20 | 6 | 15 | 11 | ASP-like protein |
| 3 | contig05709 | AAK35199.1 | *C. punctata* | 3E−94 | 188 | 20 | 6 | 15 | 11 | ASP-like protein |
| 4 | contig05709 | AAK35199.1 | *C. punctata* | 3E−94 | 249 | 20 | 6 | 15 | 17 | ASP-like protein |
| 5 | contig55746 | AAO63577.1 | *A. caninum* | 2E−08 | 83 | 12 | 1 | 13 | 12 | Secr. Prot. 5 prec. |
| 6 | isotig14500 | XP_003096841.1 | *C. remanei* | 4E−29 | 43 | 16 | 11 | 24 | 4 | Innexin |
| 7 | isotig09291 | CAD20737.1 | *O. ostertagi* | 5E−133 | 89 | 38 | 8 | 16 | 13 | Thioredoxin per. |
| 8 | isotig32303 | | | | 86 | 32 | 3 | 8 | 32 | / |
| 9 | isotig10739 | | | | 108 | 12 | 2 | 15 | 12 | / |
| 10 | isotig25459 | AAD09212.1 | *C. oncophora* | 2E−10 | 115 | 24 | 4 | 11 | 11 | 14-kDa ES prot |
| 11 | isotig09711 | AAD09213.1 | *C. oncophora* | 7E−62 | 189 | 52 | 18 | 35 | 12 | ES antigen 2 prot |
| 12 | AAD09213.1 | AAD09213.1 | *C. oncophora* | 0 | 128 | 38 | 5 | 10 | 15 | ES antigen 2 prot |
| 13 | isotig11584 | CAC38986.1 | *C. oncophora* | 3E−13 | 85 | 10 | 1 | 17 | 10 | ES antigen 1 |
| 14 | isotig11583 | CAC38986.1 | *C. oncophora* | 3E−13 | 148 | 42 | 8 | 10 | 26 | ES antigen 1 |
| 15 | isotig14336 | CAC38986.1 | *C. oncophora* | 5E−20 | 192 | 35 | 11 | 5 | 19 | ES antigen 1 |
| 16 | contig45229 | CAC38986.1 | *C. oncophora* | 2E−21 | 100 | 35 | 6 | 9 | 8 | ES antigen 1 |
| 17 | No ID | | | | | | | | | |
| 18 | CAC38986.1 | CAC38986.1 | *C. oncophora* | 0 | 160 | 53 | 7 | 4 | 34 | ES antigen 1 |
| 19 | isotig09711 | AAD09213.1 | *C. oncophora* | 7E−62 | 189 | 52 | 15 | 38 | 12 | ES antigen 2 protein |
| 20 | isotig17160 | CAC38986.1 | *C. oncophora* | 1E−13 | 90 | 41 | 4 | 14 | 8 | ES antigen 1 |
| 21 | isotig26364 | CAC38986.1 | *C. oncophora* | 9E−91 | 74 | 46 | 5 | 6 | 23 | ES antigen 1 |
| 22 | No ID | | | | | | | | | |
| 23 | isotig10740 | | | | 162 | 32 | 5 | 11 | 13 | / |
| 24 | isotig25459 | AAD09212.1 | *C. oncophora* | 2E−10 | 37 | 10 | 1 | 14 | 10 | 14-kDa ES protein |
| 25 | No ID | | | | | | | | | |

TABLE S2

MS identification of protein bands found in the three SEC fractions.

| Band N° | In-house database ID | GenBank Acc. N° | Organism (closest homology) | E-value BLASTP | MALDI-MS Mowse score | MS sequence coverage (%) | Matched peptides | Un-matched peptides | MS² sequence coverage (%) | Description (top BLASTP hit) |
|---|---|---|---|---|---|---|---|---|---|---|
| 1 | contig05709 | AAK35199.1 | *C. punctata* | 3E−94 | 315 | 17 | 5 | 16 | 17 | ASP-like protein |
| 2 | contig63173 | AAK35185.1 | *C. punctata* | 1E−89 | 245 | 35 | 7 | 19 | 15 | ASP-like protein |
| 3 | contig05709 | AAK35199.1 | *C. punctata* | 3E−94 | 276 | 30 | 8 | 13 | 19 | ASP-like protein |
| 4 | isotig24792 | XP-003114672.1 | *C. remanei* | 5E−13 | 59 | 9 | 2 | 19 | 8 | Hypothetical protein |
| 5 | isotig01086 | NP-509242.1 | *C. elegans* | 4E−119 | 345 | 50 | 22 | 15 | 16 | Aldose reductase |
| 6 | isotig13456 | AAO63577.1 | *A. caninum* | 1E−09 | 180 | 12 | 1 | 14 | 12 | Secreted protein 5 prec. |

TABLE S2-continued

MS identification of protein bands found in the three SEC fractions.

| Band N° | In-house database ID | GenBank Acc. N° | Organism (closest homology) | E-value BLASTP | MALDI-MS Mowse score | MS sequence coverage (%) | Matched peptides | Un-matched peptides | MS² sequence coverage (%) | Description (top BLASTP hit) |
|---|---|---|---|---|---|---|---|---|---|---|
| 7 | isotig13456 | AAO63577.1 | A. caninum | 1E−09 | 154 | 12 | 1 | 14 | 12 | Secreted protein 5 prec. |
| 8 | isotig00466 | ADN00784.1 | H. contortus | 4E−53 | 61 | 65 | 11 | 7 | 0 | Par. stage specif. prot. 2 |
| 9 | isotig32303 | | | | 75 | 18 | 2 | 9 | 7 | / |
| 10 | isotig11584 | CAC38986.1 | C. oncophora | 3E−13 | 119 | 13 | 3 | 15 | 10 | ES antigen 1 |
| 11 | isotig21044 | AAK35204.1 | C. punctata | 7E−18 | 159 | 33 | 7 | 10 | 12 | 14-kDa ES protein |
| 12 | CAC38986.1 | CAC38986.1 | C. oncophora | 0 | 125 | 23 | 1 | 10 | 23 | ES antigen 1 |

2.2. Multi-Protein Complexes in the Adult ES Proteome

Whereas the reducing conditions applied in 2D-GE hampered its observation, intriguingly, when comparing reducing to non-reducing 1D-GE migration profiles, traces of disulfide bridge-based oligomeric species were shown to be present in the HMW protein fraction. This finding was corroborated upon further one-dimensional native gel electrophoretic analysis. As no peptides other than those originating from double-domain ASP were noted upon MALDI-MS analysis (Table S2) and lower percentage polyacrylamide gel electrophoresis of this oligomeric species demonstrated its approx. 140 kDa molecular weight, we conclude a homo-dimeric double-domain ASP conformation for this low-abundance protein population.

2.3. Vaccination of Calves with the HMW ES Subfraction

Upon conducting the vaccination trial we recorded the time-dependent mean egg-count per gram faeces (EPG) evolution for the HMW group, as displayed in FIG. 2. When compared to the control group, the egg counts for the HMW vaccinated group was dramatically lower (P<0.01) for the entire duration of the experiment, yielding mean EPG reduction levels as high as 91% (Table 2). Whereas worm burden post necropsy was found to not differ significantly between the HMW and the control groups, the HMW group did show significantly higher percentages of inhibited L4 larvae (29.4%) (Table 2). Finally, female and male adult worm length was assessed, with those found in the HMW-treated animals measured as considerably smaller when compared to the control group (P<0.05; Table 2).

Figure 4:
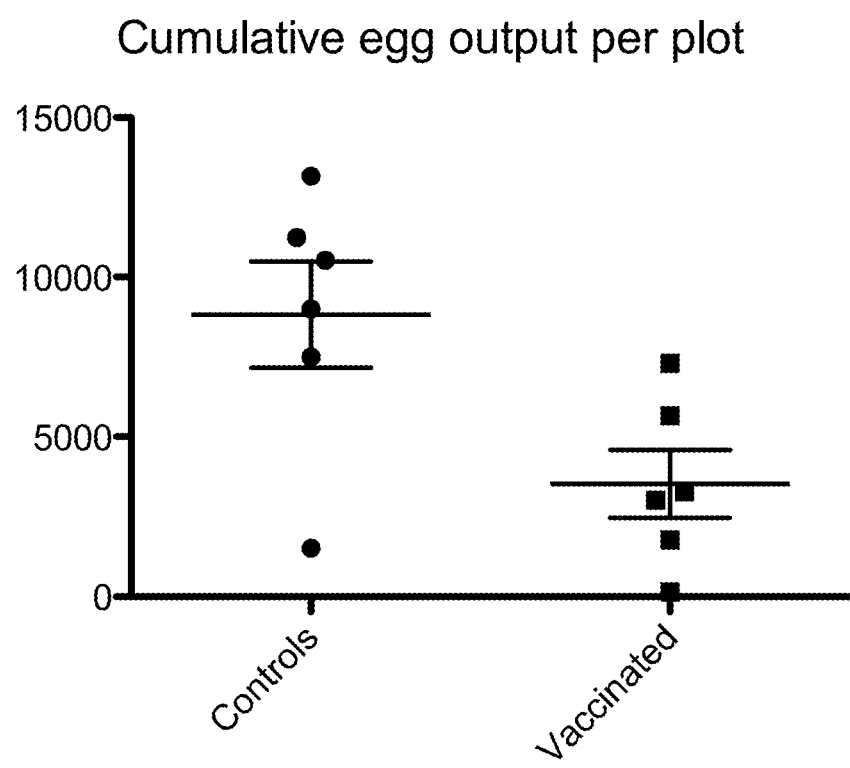
FIG. 4. Mean EPG output post-infection in the field trial. *C. oncophora* eggs per gram faeces were recorded for the groups vaccinated with adjuvant (control) and the High Molecular Weight (HMW) ES fraction.

FIG. 4 shows the cumulative C. oncophora egg counts for the field trial after a period of 5 months on pasture and again demonstrates that the egg counts for the HMW vaccinated group is significantly lower (70% reduction) compared to the control group. Individual data for the field trial are as follows:

| Controls | Vaccinated |
|---|---|
| 1519 | 5673 |
| 11246 | 3278 |
| 9011 | 138 |
| 13167 | 7311 |
| 10533 | 3022 |
| 7505 | 1776 |

TABLE 2

Overview of parasitological parameters obtained during and after the vaccination trial.

| Group | n | EPG | Worm count | % L4 | Worm length (mm) |
|---|---|---|---|---|---|
| Control | 7 | 7110 (1100-13200) | 6600 (550-12200) | 1.68 (0-8.43) | F: 12.5 (10.7-13.2) M: 9.50 (8.52-10.1) |
| HMW | 7 | 656 (0-1380) | 3370 (200-6050) | 29.4 (6.61-100) | F: 10.4 (9.66-12.4)* M: 8.40 (7.50-9.68)* | n, number of animals;

EPG, mean cumulative egg counts;

% L4, percentage of L4 worms observed in post-necropsy worm counting.

All values represent arithmetic means (+ experimentally observed range).

*P < 0.05,

**P < 0.01;

F, female;

M, male.

2.4. Immune Responses

Figure 3:
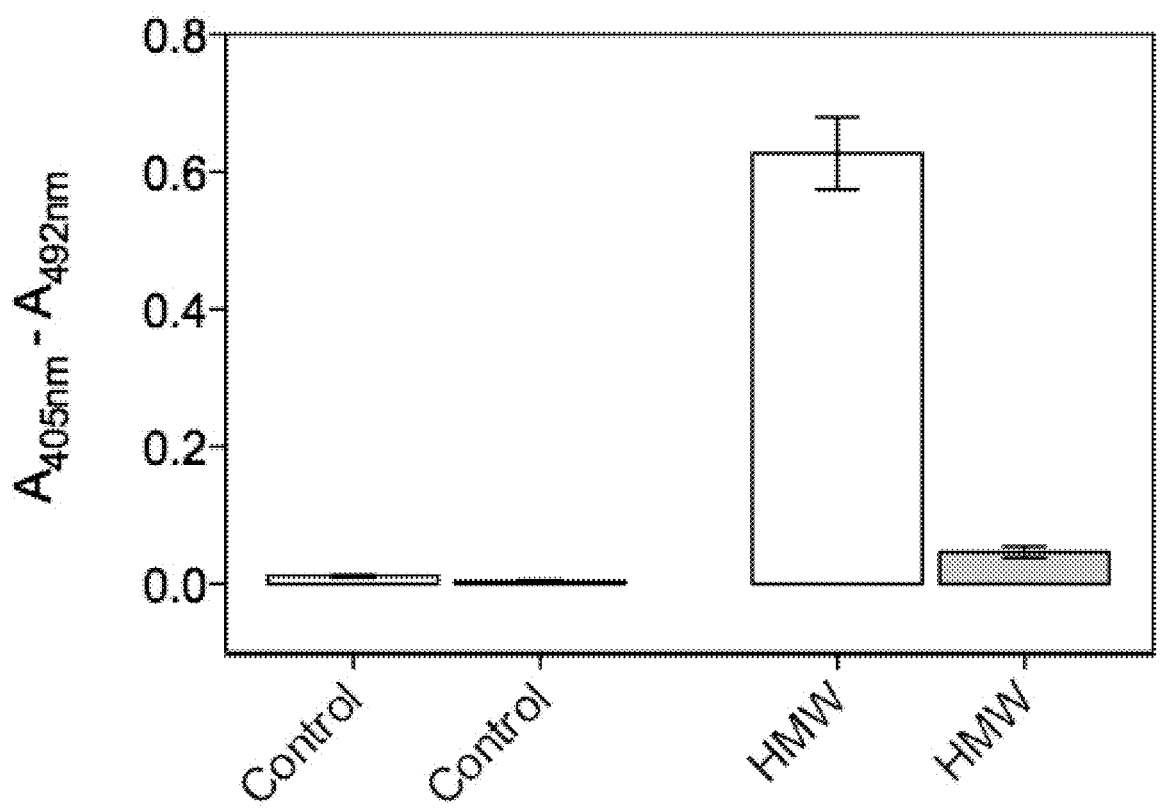
FIG. 3. Serum immunoglobulin G1 and G2 responses against *C. oncophora* antigens. Levels of serum IgG1 (white bars) and IgG2 (grey bars) against *C. oncophora* antigens, present in the HMW ES fraction, are provided as enzyme-linked immunosorbent assay (ELISA)-readouts. Statistically significant differences compared to the control group are indicated by an asterisk (*) (P<0.01).

When compared to the control group, the HMW ES subfraction was found to cause significantly higher levels of *Cooperia*-specific IgG1 levels in serum of correspondingly immunized animals (P<0.01) (FIG. 3). Additionally, although IgG2 levels were consistently much lower (approx. 15-fold) when compared to IgG1 intensities, the HMW fraction was nevertheless shown to bear significantly higher amounts of IgG2 (P<0.01), relative to the control group.

2.5. Determination and in silico Characterization of Full-Length Amino Acid Sequences Even though the complete *Cooperia oncophora* genome is yet to be fully unravelled, the recently obtained *C. oncophora* transcriptome database [33] offered a more than adequate alternative as, after having employed it in MS-directed protein identification, we were able to extend those obtained contig/isotig sequences by aligning them to overlapping ones, continuing until start and stop codons were reached. This approach proved successful for nine out of the eventually twelve different proteins present in the adult *C. oncophora* excretome/secretome (Table 1). For two proteins, more specifically the HMW hypothetical protein (isotig27828; highest homology to the *Caenorhabditis remanei* hypothetical protein; GenBank accession number XP_003114672) and innexin (isotig12080; highest homology to the *C. remanei* innexin; GenBank accession number XP_003096841.1), we were unable to extend their sequences until full-length and, based on homology in other species, they are expected to lack 733 and 160 amino acids at their N-termini, respectively. Lastly, whereas mass spectrometric analyses initially identified only peptides from the C-terminal domain of the double-domain ASP, by applying PCR techniques we were able to reveal its sequence until quasi full-length, that is, based on its *Cooperia punctata* homologue (AAK35199.1), apart from a 21-residue signal peptide. The N- and C-termini of the identified double domain ASP consist of the amino acids LCSLDNGMT (SEQ ID NO: 14) and DEDCKCSSCRCSTQLSMCINPN (SEQ ID NO: 15), respectively.

As an initial crude in silico characterization, software-driven signal sequence prediction, combined with N-linked glycosylation consensus site searches, revealed only the double- and single-domain ASPs and the LMW ES antigens as potentially carrying sugar moieties (Table 1). Further in silico analysis of the obtained full-length sequences yielded molecular weight values corresponding well to those observed in-gel.

2.6. Glycan Analysis of the *Cooperia oncophora* ES Proteome

Overall ES glycosylation was studied by MALDI-TOF MS analysis upon release of the N- and O-linked glycan moieties. Whereas a clear set of PNGase F-released glycans was detected, no signals could be detected in the PNGase A-specific release (data not shown), thereby indicating that no significant amounts of N-glycans with 1-3-linked fucose modifications of the asparagine-linked N-acetylglucosamine (GlcNAc) are present in the excretome/secretome of adult *C. oncophora*. Regarding the O-glycan preparation, only minor signals were detected (data not shown). To obtain more information on the presence of glycan moieties on specific proteins in the *C. oncophora* ES fraction, the N- and O-glycans, released from the LMW, MMW and HMW protein clusters, were analyzed by MALDI-time-of-flight (TOF) mass spectrometry. Whereas no significant amounts of N-glycans could be detected in the LMW and HMW fractions, the major N-glycan signals observed in the total ES pool were also found to be present in the MMW N-glycan spectrum. On the other hand, marginal levels of O-glycan signals were detected in the HMW fraction exclusively. However, these signals could not be assigned to common O-glycan structures (not even putatively) and therefore were not further investigated.

Using the monoisotopic mass of each of the N-glycan peaks observed, monosaccharide compositions were assigned and putative structures deduced. Major signals detected in the spectrum of MMW N-glycans that also appeared in the total ES N-glycan spectrum were derived from glycan moieties with the compositions F1H3N2, H5N2, H6N2 and H7N2 at m/z values 1176.4, 1354.4, 1516.5 and 1678.5 [M-H]$^-$, respectively (F, fucose, Fuc; H, hexose, Hex; N, N-acetylhexosamine, HexNAc). These compositions are indicative for a paucimannosidic, core-fucosylated glycan (F1H3N2) and a series of oligomannose glycans Man$_{5-7}$GlcNAc$_2$ (Man, mannose). To confirm these assignments a sample of the MMW N-glycans was incubated with α-mannosidase, leading to a spectrum containing detectable signals only at m/z 706.3 and 852.3 for H1N2 (Man1GlcNAc2) and F1H1N2 (Fuc1Man1GlcNAc2), thereby confirming the presence of the mannose extensions in the untreated sample.

Prompted by the presence of a putative N-glycosylation site in the single-domain ASP in the MMW protein cluster (Table I), we subjected the tryptic glycopeptides derived from the corresponding single-domain ASP gel slice to nano-liquid chromatography (LC) MS/MS analysis. The obtained data were interrogated for the presence of glycosylated peptides by searching for MS/MS spectra containing the common glycan fragment ions H1N1 (m/z 366.1 [M+H]$^+$) and H2N1 (m/z 528.2 [M+H]$^+$). Interestingly, a series of parent ions was detected that could be assigned to the H5N2, H6N2 and H7N2 glycoforms of the single-domain ASP tryptic peptide WNCTLEAK (1021.5 [M+H]$^+$, with cysteine as carbamidomethyl derivative) based on: i) the overall mass of the glycopeptide, and ii) the collision induced dissociation fragment spectra showing the fragmentation patterns of the glycosidic linkages in each peptide glycoform. An overview of detected and fragmented glycopeptide moieties derived from the same gel slice is provided in Table S3. From the parent ion m/z 1201.1 [M+2H]$^{2+}$ a clear series of [M+H]$^{2+}$ fragment ions indicate the loss of six hexose residues and one N-acetylhexosamine (HexNAc), leaving the corresponding peptide-fragment ion with a single N-acetyl-glucosamine (GlcNAc) residue linked to the asparagine residue at m/z 612.8. Similar (but less intense) spectra were obtained for the H5N2 and H7N2 glycoforms of the same peptide, indicating that the Man$_{5-7}$GlcNAc$_2$ N-glycans released from MMW proteins are present on a single glycosylation site of the single-domain ASP.

TABLE S3

Glycopeptide variants detected in the tryptic digest of the single-domain ASP, analyzed by MS/MS. Different glycoforms in line with the MMW ES N-glycan profile were detected, with H5N2 and H6N2 glycoforms giving rise to the highest ion intensities.

| Parent Ion Detected | Ion Charge | Peptide | Seq ID | Missed cleavages | Glycan |
|---|---|---|---|---|---|
| 727.7 | $[M + 3H]^{3+}$ | LRWNCTLEAK | 9 | 1 | H3N2 |
| 800.7 | $[M + 3H]^{3+}$ | WNCTLEAK | 10 | 0 | H6N2 |
| 836.4 | $[M + 3H]^{3+}$ | LRWNCTLEAK | 9 | 1 | H5N2 |
| 876.4 | $[M + 3H]^{3+}$ | WNCTLEAKAR | 11 | 1 | H6N2 |
| 890.4 | $[M + 3H]^{3+}$ | LRWNCTLEAK | 9 | 1 | H6N2 |
| 957.4 | $[M + 3H]^{2+}$ | WNCTLEAK | 10 | 0 | H3N2 |
| 1038.4 | $[M + 3H]^{2+}$ | WNCTLEAK | 10 | 0 | H4N2 |
| 1119.9 | $[M + 3H]^{2+}$ | WNCTLEAK | 10 | 0 | H5N2 |
| 1200.0 | $[M + 3H]^{2+}$ | WNCTLEAK | 10 | 0 | H6N2 |
| 1281.5 | $[M + 3H]^{2+}$ | WNCTLEAK | 10 | 0 | H7N2 |

3. Discussion

Combining the MALDI-MS-obtained identifications from both two-dimensional gel electrophoretic and size exclusion chromatographic fractionation of the adult-stage *Cooperia oncophora* excretome/secretome yielded twelve different proteins distributed over three distinct molecular weight clusters (Table 1). Whereas a total of twelve proteins may appear as modest when compared to the ES fractions of other helminths such as *Ascaris suum* (41), *Schistosoma japonicum* (42) and *Haemonchus contortus* (43), often revealing up to a hundred or more different proteins in their excretome/secretome, such quantitative differences may arise from a combination of: i) the host-worm interface differing substantially between parasites and thus posing specific challenges during infection, and ii) the excretome/secretome of some helminths having already been further developed, with potentially redundant proteins eliminated and/or crucial high-activity proteins having been enriched. Nevertheless, although a number of proteins with unknown functions were identified, the excretome/secretome from adult *C. oncophora* also bears a set of proteins that have previously been noted in other nematodes/helminths and whose functions have been (partially) elucidated. Among those we find aldose reductase and thioredoxin peroxidase, two proteins known as being involved in detoxification mechanisms, the first converting the mutagenic and toxic methylglyoxal, a by-product of glycolysis, into acetol (44), and the latter acting as an antioxidant which eliminates reactive oxygen species generated during oxygen metabolism, oxidative processes and host immune responses (45). Another documented protein that was identified from the adult *C. oncophora* ES fraction is innexin (Pfam: PF00876), an invertebrate equivalent to the connexin family of molecules. These are gap-junction proteins that, upon oligomerization, form intercellular channels through which ions and small molecules may pass, thereby allowing intercellular communication (46).

Apart from two as of yet non-annotated molecules (isotig32303 and isotig10739), we additionally revealed the low molecular weight spot cluster (LMW) as essentially consisting of three different proteins, i.e. 14-kDa ES protein, ES antigen 1 and ES antigen 2 protein. Strikingly, although functionally still poorly characterized, this set of proteins has previously seen its *Cooperia punctata* equivalents suggested as potential vaccine candidates (47), however, no reports of a successful outcome have been published. Why these proteins display such extensive diversity, as seen in their 2D-GE spot profile, remains elusive, but it has been hypothesized that this may create antigenic diversity and/or a set of redundant proteins which may be eliminated through the host immune response without serious detrimental effects on parasite viability (47).

Interestingly, both the HMW and MMW fractions were found to have one type of protein in common, that is, they each harbour an activation-associated secreted protein (ASP). Such proteins constitute a Strongylida-specific subgroup of the CAP protein superfamily (also termed sperm-cell glycoprotein/Tpx-1/Ag5/PR- 1/Sc7 (SCP/TAPS) proteins; Pfam PF00188), which displays an extreme diversity both in occurrence, covering prokaryotes and eukaryotes, and function, having been shown to be involved in processes as diverse as reproduction, cancer and immune regulation [48]. To date, however, the true biological function of ASPs still remains enigmatic, despite substantial efforts having recently been made [49-54], and even though research in that particular field is still in its infancy, some ASPs have been tested in vaccination trials, both in their native and recombinant forms [55-58]. As of yet, ASPs have been found in three configurations: i) as double domain ASPs, composed of two distinct but related CAP domains, ii) as C-type single domain ASPs, and iii) as N-type single domain ASPs, the second and the latter bearing the highest homology to the C- and N-terminus of the double domain ASPs, respectively [51]. Our study of the adult *C. oncophora* excretome/secretome yielded a double-domain ASP as part of the HMW cluster, and a single-domain ASP, belonging to the MMW group (Table 1). Whereas the double-domain ASP was predicted to carry a signal sequence and bears two consensus acceptor sites for N-linked glycosylation, it was revealed not to carry any such moieties. Furthermore, upon 2D-GE analysis, a train of four distinct spots was observed, all of which correspond to this double-domain ASP, reflecting a level of sequence diversity, as is further disclosed herein. Whereas unnoticed upon 2D-GE analysis, the one-dimensional gel migration pattern for the double-domain ASP showed a doublet both under reducing and non-reducing conditions. Since it does not carry any sugar moieties, this observation may be attributed to partial processing of the signal peptide. Perhaps the most surprising observation regarding this double-domain ASP was a small portion of it migrating as a dimer, exclusively upon non-reducing gel electrophoresis, thereby implying it to be disulfide bridge-based. Whereas single-domain ASPs are known to dimerize in solution [49], these are the first indications of a double-domain ASP mimicking this behaviour.

In contrast to its double-domain counterpart, the single-domain ASP, as found in the MMW protein cluster, displayed no signs of detectable sequence diversity or oligomerization. Interestingly, corroborating in silico predictions in terms of signal sequence and N-glycosylation consensus sites, the single-domain ASP was indeed shown to carry an N-linked glycan moiety at Asn93. Although its general impact on protein structure and immunogenicity is still to be conclusively determined, the structure of the glycan group was found to resemble that of the *Ostertagia ostertagi* single-domain ASP [53], the crystal structure of which was recently solved and suggests a modest structural role for the glycan moiety. Analogous to the double-domain ASP, upon one-dimensional gel electrophoretic analysis of the single-domain ASP a doublet of bands was observed with the lower molecular weight band much less abundant when compared to the double-domain ASP situation where both bands of the doublet were quasi equally intense. Possibly, the lower single-domain ASP band represents the protein devoid of its Asn93-linked glycan moiety.

Our vaccination trial showed that the HMW protein fraction, essentially consisting of the double-domain ASP, is particularly useful for vaccine development, with EPG reduction levels surpassing 90%, drastically inhibited L4 larvae and substantial decreases in worm length when compared to the control group (Table 2). Moreover, in serum of immunized calves IgG1 levels are elevated upon its administration, with also a marginal IgG2 response (FIG. 3). Finally, vaccination with the HMW fraction conferred protection against a natural infection with *Cooperia oncophora* in a field trial.

In conclusion, the double-domain ASP yields substantial protection levels and displays low complexity in terms of post-translational modifications, thereby facilitating its recombinant up-scaling process. As noted above, the efficacious HMW fraction employed in the vaccine trial consisted mostly of the double-domain ASP and is a preferred *Cooperia oncophera* vaccine component.

REFERENCES

1. Kloosterman, A., Albers, G. A., and van den Brink, R. (1984) Negative interactions between Ostertagia ostertagi and *Cooperia oncophora* in calves. *Vet Parasitol* 15, 135-150.
2. Coles, G. C., and Klei, T. R. (1995) Animal parasites, politics and agricultural research. *Parasitol Today* 11, 276-278.
3. Michel, J. F. (1976) The epidemiology and control of some nematode infections in grazing animals. *Adv Parasitol* 14, 355-397.
4. Lawrence, J. D. a. I., M.A. (2007) Economic analysis of pharmaceutical technologies in modern beef production. *NCCC-134 meeting on Applied Commodity Price Analysis, Forecasting and Market Risk Management*, April 16-17, 2007, Chicago.
5. Anziani, O. S., Suarez, V., Guglielmone, A. A., Warnke, O., Grande, H., and Coles, G. C. (2004) Resistance to benzimidazole and macrocyclic lactone anthelmintics in cattle nematodes in Argentina. *Vet Parasitol* 122, 303-306.
6. Condi, G. K., Soutello, R. G., and Amarante, A. F. (2009) Moxidectin-resistant nematodes in cattle in Brazil. *Vet Parasitol* 161, 213-217.
7. Demeler, J., Van Zeveren, A. M., Kleinschmidt, N., Vercruysse, J., Hoglund, J., Koopmann, R., Cabaret, J., Claerebout, E., Areskog, M., and von Samson-Himmelstjerna, G. (2009) Monitoring the efficacy of ivermectin and albendazole against gastro intestinal nematodes of cattle in Northern Europe. *Vet Parasitol* 160, 109-115.
8. El-Abdellati, A., Geldhof, P., Claerebout, E., Vercruysse, J., and Charlier, J. (2010) Monitoring macrocyclic lactone resistance in *Cooperia oncophora* on a Belgian cattle farm during four consecutive years. *Vet Parasitol* 171, 167-171.
9. Waghorn, T. S., Leathwick, D. M., Rhodes, A. P., Jackson, R., Pomroy, W. E., West, D. M., and Moffat, J. R. (2006) Prevalence of anthelmintic resistance on 62 beef cattle farms in the North Island of New Zealand. *N Z Vet J* 54, 278-282.
10. Bungiro, R., and Cappello, M. (2004) Hookworm infection: new developments and prospects for control. *Curr Opin Infect Dis* 17, 421-426.
11. Abraham, D., Leon, O., Leon, S., and Lustigman, S. (2001) Development of a recombinant antigen vaccine against infection with the filarial worm Onchocerca volvulus. *Infect Immun* 69, 262-270.
12. MacDonald, A. J., Tawe, W., Leon, O., Cao, L., Liu, J., Oksov, Y., Abraham, D., and Lustigman, S. (2004) Ov-ASP-1, the Onchocerca volvulus homologue of the activation associated secreted protein family is immunostimulatory and can induce protective anti-larval immunity. *Parasite Immunol* 26, 53-62.
13. Taylor, M. J., Jenkins, R. E., and Bianco, A. E. (1996) Protective immunity induced by vaccination with Onchocerca volvulus tropomyosin in rodents. *Parasite Immunol* 18, 219-225.
14. Wu, Y., Egerton, G., Pappin, D. J., Harrison, R. A., Wilkinson, M. C., Underwood, A., and Bianco, A. E. (2004) The Secreted Larval Acidic Proteins (SLAPs) of Onchocerca spp. are encoded by orthologues of the alt gene family of Brugia malayi and have host protective potential. *Mol Biochem Parasitol* 134, 213-224.
15. Islam, M. K., Miyoshi, T., and Tsuji, N. (2005) Vaccination with recombinant Ascaris suum 24-kilodalton antigen induces a Th1/Th2-mixed type immune response and confers high levels of protection against challenged Ascaris suum lung-stage infection in BALB/c mice. *Int J Parasitol* 35, 1023-1030.
16. Tsuji, N., Suzuki, K., Kasuga-Aoki, H., Isobe, T., Arakawa, T., and Matsumoto, Y. (2003) Mice intranasally immunized with a recombinant 16-kilodalton antigen from roundworm Ascaris parasites are protected against larval migration of *Ascaris suum. Infect Immun* 71, 5314-5323.
17. Tsuji, N., Suzuki, K., Kasuga-Aoki, H., Matsumoto, Y., Arakawa, T., Ishiwata, K., and Isobe, T. (2001) Intranasal 17. immunization with recombinant *Ascaris suum* 14-kilodalton antigen coupled with cholera toxin B subunit induces protective immunity to *A. suum* infection in mice. *Infect Immun* 69, 7285-7292.

18. Redmond, D. L., and Knox, D. P. (2004) Protection studies in sheep using affinity-purified and recombinant cysteine proteinases of adult *Haemonchus contortus*. *Vaccine* 22, 4252-4261.

19. Redmond, D. L., and Knox, D. P. (2006) Further protection studies using recombinant forms of Haemonchus contortus cysteine proteinases. *Parasite Immunol* 28, 213-219.

20. Winter, J. A., Davies, 0. R., Brown, A. P., Garnett, M. C., Stolnik, S., and Pritchard, D. I. (2005) The assessment of hookworm calreticulin as a potential vaccine for necatoriasis. *Parasite Immunol* 27, 139-146.

21. Lightowlers, M. W. (2006) Vaccines against cysticercosis and hydatidosis: foundations in taeniid cestode immunology. *Parasitol Int* 55 Suppl, S39-43.

22. Lightowlers, M. W., Gauci, C. G., Chow, C., Drew, D. R., Gauci, S. M., Heath, D. D., Jackson, D. C., Dadley-Moore, D. L., and Read, A. J. (2003) Molecular and genetic characterisation of the host-protective oncosphere antigens of taeniid cestode parasites. *Int J Parasitol* 33, 1207-1217.

23. Plancarte, A., Flisser, A., Gauci, C. G., and Lightowlers, M. W. (1999) Vaccination against Taenia solium cysticercosis in pigs using native and recombinant oncosphere antigens. *Int J Parasitol* 29, 643-647.

24. Hillyer, G. V. (2005) Fasciola antigens as vaccines against fascioliasis and schistosomiasis. *J Helminthol* 79, 241-247.

25. Abane, J. L., Oleaga, A., Ramajo, V., Casanueva, P., Arellano, J. L., Hillyer, G. V., and Muro, A. (2000) Vaccination of mice against schistosoma bovis with a recombinant fatty acid binding protein from Fasciola hepatica. *Vet Parasitol* 91, 33-42.

26. Boulanger, D., Schneider, D., Chippaux, J. P., Sellin, B., and Capron, A. (1999) Schistosoma bovis: vaccine effects of a recombinant homologous glutathione 5-transferase in sheep. *Int J Parasitol* 29, 415-418.

27. Boulanger, D., Trottein, F., Mauny, F., Bremond, P., Couret, D., Pierce, R. J., Kadri, S., Godin, C., Sellin, E., Lecocq, J. P., and et al. (1994) Vaccination of goats against the trematode Schistosoma bovis with a recombinant homologous schistosome-derived glutathione S-transferase. *Parasite Immunol* 16, 399-406.

28. Loukas, A., Tran, M., and Pearson, M. S. (2007) Schistosome membrane proteins as vaccines. *Int J Parasitol* 37, 257-263.

29. Pacifico, L. G., Fonseca, C. T., Chiari, L., and Oliveira, S. C. (2006) Immunization with Schistosoma mansoni 22.6 kDa antigen induces partial protection against experimental infection in a recombinant protein form but not as DNA vaccine. *Immunobiology* 211, 97-104.

30. Tran, M. H., Pearson, M. S., Bethony, J. M., Smyth, D. J., Jones, M. K., Duke, M., Don, T. A., McManus, D. P., Correa-Oliveira, R., and Loukas, A. (2006) Tetraspanins on the surface of Schistosoma mansoni are protective antigens against schistosomiasis. *Nat Med* 12, 835-840.

31. Elliott, D. E., Summers, R. W., and Weinstock, J. V. (2007) Helminths as governors of immune-mediated inflammation. *Int J Parasitol* 37, 457-464.

32. Haffner, A., Guilavogui, A. Z., Tischendorf, F. W., and Brattig, N. W. (1998) Onchocerca volvulus: microfilariae secrete elastinolytic and males nonelastinolytic matrix-degrading serine and metalloproteases. *Exp Parasitol* 90, 26-33.

33. Martin, J., Abubucker, S., Heizer, E., Taylor, C. M., and Mitreva, M. (2012) Nematode.net update 2011: addition of data sets and tools featuring next-generation sequencing data. *Nucleic Acids Res* 40, D720-728.

34. Laemmli, U. K. (1970) Cleavage of structural proteins during the assembly of the head of bacteriophage T4. *Nature* 227, 680-685.

35. Altschul, S. F., Gish, W., Miller, W., Myers, E. W., and Lipman, D. J. (1990) Basic local alignment search tool. *J. Mol Biol* 215, 403-410.

36. Bendtsen, J. D., Nielsen, H., von Heijne, G., and Brunak, S. (2004) Improved prediction of signal peptides: SignalP 3.0. *J Mol Biol* 340, 783-795.

37. Bendtsen, J. D., Jensen, L. J., Blom, N., Von Heijne, G., and Brunak, S. (2004) Feature-based prediction of non-classical and leaderless protein secretion. *Protein Eng Des Sel* 17, 349-356.

38. Ruhaak, L. R., Steenvoorden, E., Koeleman, C. A., Deelder, A. M., and Wuhrer, M. (2010) 2-picoline-borane: a non-toxic reducing agent for oligosaccharide labeling by reductive amination. *Proteomics* 10, 2330-2336.

39. Geldhof, P., Claerebout, E., Knox, D., Vercauteren, I., Looszova, A., and Vercruysse, J. (2002) Vaccination of calves against Ostertagia ostertagi with cysteine proteinase enriched protein fractions. *Parasite Immunol* 24, 263-270.

40. Yatsuda, A. P., Eysker, M., Vieira-Bressan, M. C., and De Vries, E. (2002) A family of activation associated secreted protein (ASP) homologues of Cooperia punctata. *Res Vet Sci* 73, 297-306.

41. Islam, M. K., Miyoshi, T., Yokomizo, Y., and Tsuji, N. (2004) The proteome expression patterns in adult Ascaris suum under exposure to aerobic/anaerobic environments analyzed by two-dimensional electrophoresis. *Parasitol Res* 93, 96-101.

42. Liu, F., Cui, S. J., Hu, W., Feng, Z., Wang, Z. Q., and Han, Z. G. (2009) Excretory/secretory proteome of the adult developmental stage of human blood fluke, Schistosoma japonicum. *Mol Cell Proteomics* 8, 1236-1251.

43. Yatsuda, A. P., Krijgsveld, J., Cornelissen, A. W., Heck, A. J., and de Vries, E. (2003) Comprehensive analysis of the secreted proteins of the parasite Haemonchus contortus reveals extensive sequence variation and differential immune recognition. *J Biol Chem* 278, 16941-16951.

44. Rath, J., Gowri, V. S., Chauhan, S. C., Padmanabhan, P. K., Srinivasan, N., and Madhubala, R. (2009) A glutathione-specific aldose reductase of Leishmania donovani and its potential implications for methylglyoxal detoxification pathway. *Gene* 429, 1-9.

45. Lu, W., Egerton, G. L., Bianco, A. E., and Williams, S. A. (1998) Thioredoxin peroxidase from Onchocerca volvulus: a major hydrogen peroxide detoxifying enzyme in filarial parasites. *Mol Biochem Parasitol* 91, 221-235.

46. Phelan, P., Bacon, J. P., Davies, J. A., Stebbings, L. A., Todman, M. G., Avery, L., Baines, R. A., Barnes, T. M., Ford, C., Hekimi, S., Lee, R., Shaw, J. E., Starich, T. A., Curtin, K. D., Sun, Y. A., and Wyman, R. J. (1998) Innexins: a family of invertebrate gap-junction proteins. *Trends Genet* 14, 348-349.

47. Yatsuda, A. P., De Vries, E., Vieira Bressan, M. C., and Eysker, M. (2001) A *Cooperia punctata* gene family encoding 14 kDa excretory-secretory antigens conserved for trichostrongyloid nematodes. *Parasitology* 123, 631-639.

48. Gibbs, G. M., Roelants, K., and O'Bryan, M. K. (2008) The CAP superfamily: cysteine-rich secretory proteins, antigen 5, and pathogenesis-related 1 proteins--roles in reproduction, cancer, and immune defense. *Endocr Rev* 29, 865-897.

49. Asojo, O. A. (2011) Structure of a two-CAP-domain protein from the human hookworm parasite Necator americanus. *Acta Crystallogr D Biol Crystallogr* 67, 455-462.

50. Asojo, O. A., Goud, G., Dhar, K., Loukas, A., Zhan, B., Deumic, V., Liu, S., Borgstahl, G. E., and Hotez, P. J. (2005) X-ray structure of Na-ASP-2, a pathogenesis-related-1 protein from the nematode parasite, Necator americanus, and a vaccine antigen for human hookworm infection. *J Mol Biol* 346, 801-814.

51. Geldhof, P., Vercauteren, I., Gevaert, K., Staes, A., Knox, D. P., Vandekerckhove, J., Vercruysse, J., and Claerebout, E. (2003) Activation-associated secreted proteins are the most abundant antigens in a host protective fraction from *Ostertagia ostertagi. Mol Biochem Parasitol* 128, 111-114.

52. Hawdon, J. M., Jones, B. F., Hoffman, D. R., and Hotez, P. J. (1996) Cloning and characterization of Ancylostoma-secreted protein. A novel protein associated with the transition to parasitism by infective hookworm larvae. *J Biol Chem* 271, 6672-6678.

53. Meyvis, Y., Callewaert, N., Gevaert, K., Timmerman, E., Van Durme, J., Schymkowitz, J., Rousseau, F., Vercruysse, J., Claerebout, E., and Geldhof, P. (2008) Hybrid N-glycans on the host protective activation-associated secreted proteins of Ostertagia ostertagi and their importance in immunogenicity. *Mol Biochem Parasitol* 161, 67-71.

54. Osman, A., Wang, C. K., Winter, A., Loukas, A., Tribolet, L., Gasser, R. B., and Hofmann, A. (2011) Hookworm SCP/TAPS protein structure-A key to understanding host-parasite interactions and developing new interventions. *Biotechnol Adv.*

55. Geldhof, P., Meyvis, Y., Vercruysse, J., and Claerebout, E. (2008) Vaccine testing of a recombinant activation-associated secreted protein (ASP1) from *Ostertagia ostertagi. Parasite Immunol* 30, 57-60.

56. Goud, G. N., Zhan, B., Ghosh, K., Loukas, A., Hawdon, J., Dobardzic, A., Deumic, V., Liu, S., Dobardzic, R., Zook, B. C., Jin, Q., Liu, Y., Hoffman, L., Chung-Debose, S., Patel, R., Mendez, S., and Hotez, P. J. (2004) Cloning, yeast expression, isolation, and vaccine testing of recombinant Ancylostoma-secreted protein (ASP)-1 and ASP-2 from Ancylostoma ceylanicum. *J Infect Dis* 189, 919-929.

57. Mendez, S., Zhan, B., Goud, G., Ghosh, K., Dobardzic, A., Wu, W., Liu, S., Deumic, V., Dobardzic, R., Liu, Y., Bethony, J., and Hotez, P. J. (2005) Effect of combining the larval antigens Ancylostoma secreted protein 2 (ASP-2) and metalloprotease 1 (MTP-1) in protecting hamsters against hookworm infection and disease caused by Ancylostoma ceylanicum. *Vaccine* 23, 3123-3130.

58. Meyvis, Y., Geldhof, P., Gevaert, K., Timmerman, E., Vercruysse, J., and Claerebout, E. (2007) Vaccination against Ostertagia ostertagi with subfractions of the protective ES-thiol fraction. *Vet Parasitol* 149, 239-245.

59. Geldhof, P., De Maere, V., Vercruysse, J., Claerebout, E. Recombinant expression systems: the obstacle to helminth vaccines? *Trends in Parasitology* 2007 23:527-532

60. J Clin Microbiol. 1997 Jul;35(7):1728-33. Use of cloned excretory/secretory low-molecular-weight proteins of *Cooperia oncophora* in a serological assay. Poot J, Kooyman F N, Dop P Y, Schallig H D, Eysker M, Cornelissen A W.

61. Int J Parasitol. 2003 Nov;33(13):1503-14. T-cell mediated immune responses in calves primary-infected or re-infected with *Cooperia oncophora* : similar effector cells but different timing. Kanobana K, Koets A, Bakker N, Ploeger H W, Vervelde L.

62. Panicali et al; PNAS USA 79, 4927 (1982).

63. Goeddel, et al., Nucl. Acids Res., 8, 4057 (1980).

64. Chang, et al., Nature, 275, 615 (1978).

65. Nakamura, K. and Inouge, M., EMBO J., 1, 771-775 (1982).

66. Remaut, E. et al., Nucl. Acids Res., 11, 4677-4688 (1983).

67. Nat Biotechnol. 2002 Dec;20(12):1265-8. Epub 2002 November 4. Boosting heterologous protein production in transgenic dicotyledonous seeds using Phaseolus vulgaris regulatory sequences. De Jaeger G, Scheffer S, Jacobs A, Zambre M, Zobell O, Goossens A, Depicker A, Angenon G.

68. Jacobs et al., Nature protocols 2009 4:58-70.

69. Valerio, D. et al.; in Baum, S. J., Dicke, K. A., Lotzova, E. and Pluznik, D. H. (Eds.), Experimental Haematology today-1988. Springer Verlag, N.Y.: pp. 92-99 (1989).

---

What is claimed is:

1. An isolated complementary DNA ("cDNA") nucleic acid sequence encoding a *Cooperia oncophora* protein or immunogenic fragment of the protein, wherein the protein or immunogenic fragment thereof comprises an amino acid sequence having a sequence identity of at least 85% to the amino acid sequence of SEQ ID NO: 1.

2. The cDNA nucleic acid sequence according to claim 1, having at least 85% sequence identity with the nucleic acid sequence of SEQ ID NO: 2.

3. The cDNA nucleic acid sequence according to claim 1, having at least 90% sequence identity with the nucleic acid sequence of SEQ ID NO: 2.

4. A recombinant DNA molecule comprising the nucleic acid sequence according to claim 2 and a functionally linked promoter.

5. A vector comprising the nucleic acid sequence according to claim 2.

6. The vector according to claim 5, wherein the vector is chosen from a plasmid, bacteriophage, cosmid, virus, or minichromosome.

7. A vector comprising the recombinant DNA molecule according to claim 4.

8. A host cell comprising the nucleic acid sequence according to claim 2.

9. A host cell comprising the recombinant DNA molecule according to claim 4.

10. A host cell comprising the vector according to claim 7.

11. The host cell according to claim 8, wherein the host cell is chosen from an animal cell, bacterial cell, yeast cell, insect cell, or plant cell.

* * * * *

UNITED STATES PATENT AND TRADEMARK OFFICE
CERTIFICATE OF CORRECTION

PATENT NO. : 10,946,077 B2
APPLICATION NO. : 16/126536
DATED : March 16, 2021
INVENTOR(S) : Peter Geldhof et al.

Page 1 of 1

It is certified that error appears in the above-identified patent and that said Letters Patent is hereby corrected as shown below:

In the Specification

In Column 23, row 6 & Column 2, table S3, delete "[M+3H]$^{2+}$" and insert --[M+2H]$^{2+}$--, therefor.

In Column 23, row 7 & Column 2, table S3, delete "[M+3H]$^{2+}$" and insert --[M+2H]$^{2+}$--, therefor.

In Column 23, row 8 & Column 2, table S3, delete "[M+3H]$^{2+}$" and insert --[M+2H]$^{2+}$--, therefor.

In Column 23, row 9 & Column 2, table S3, delete "[M+3H]$^{2+}$" and insert --[M+2H]$^{2+}$--, therefor.

In Column 23, row 10 & Column 2, table S3, delete "[M+3H]$^{2+}$" and insert --[M+2H]$^{2+}$--, therefor.

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*